US012758493B2

(12) United States Patent
Smith et al.

(10) Patent No.: US 12,758,493 B2
(45) Date of Patent: Oct. 13, 2026

(54) LAYERED EDIBLE PRODUCT FOR MULTI-STAGE DOSING OF MULTI-FUNCTION ACTIVE PHARMACEUTICAL INGREDIENTS

(71) Applicant: Transport Authority, Inc., Dover, DE (US)

(72) Inventors: Walter Lee Smith, Danville, CA (US); William Warren, Lafayette, CA (US)

(73) Assignee: TRANSPORT AUTHORITY, INC., San Leandro, CA (US)

( * ) Notice: Subject to any disclaimer, the term of this patent is extended or adjusted under 35 U.S.C. 154(b) by 638 days.

(21) Appl. No.: 18/170,873

(22) Filed: Feb. 17, 2023

(65) Prior Publication Data

US 2023/0263726 A1 Aug. 24, 2023

Related U.S. Application Data

(60) Provisional application No. 63/311,893, filed on Feb. 18, 2022.

(51) Int. Cl.

*A61K 9/00* (2006.01)
*A61K 31/00* (2006.01)
*A61K 31/05* (2006.01)
*A61K 31/352* (2006.01)

(52) U.S. Cl.

CPC ............ *A61K 9/0056* (2013.01); *A61K 31/05* (2013.01); *A61K 31/352* (2013.01); *A61K 31/658* (2023.05)

(58) Field of Classification Search

CPC .... A61K 9/0056; A61K 31/05; A61K 31/352; A61K 9/006; A61K 9/2086

See application file for complete search history.

(56) References Cited

U.S. PATENT DOCUMENTS

| | | | |
|---|---|---|---|
| 4,322,449 | A | 3/1982 | Voss et al. |
| 7,090,858 | B2 | 8/2006 | Jayaraman |
| 7,325,548 | B2 | 2/2008 | Enslin |
| 7,900,850 | B2 | 3/2011 | Zengerle et al. |
| 8,071,049 | B2 | 12/2011 | Koltay et al. |
| 8,910,630 | B2 | 12/2014 | Todd |
| 9,380,813 | B2 | 7/2016 | Mccullough |
| 9,474,304 | B2 | 10/2016 | Born et al. |
| 9,526,792 | B1 | 12/2016 | Degeeter |
| 9,854,828 | B2 | 1/2018 | Langeland |
| 9,937,147 | B2 | 4/2018 | Degeeter |
| 9,974,333 | B1 | 5/2018 | Disner |
| 10,239,069 | B2 | 3/2019 | Rogers |
| 10,265,362 | B2 | 4/2019 | Schaneville |
| 10,369,178 | B2 | 8/2019 | Greenbaum et al. |
| 10,383,358 | B2 | 8/2019 | Kaplan et al. |
| 10,485,373 | B1 | 11/2019 | Millikin et al. |
| 10,772,837 | B2 | 9/2020 | Lefler et al. |
| 2004/0086603 | A1 | 5/2004 | Shastry et al. |
| 2007/0141198 | A1 | 6/2007 | Yang |
| 2008/0160787 | A1 | 7/2008 | Lehmann |
| 2009/0181080 | A1 | 7/2009 | Kottayil et al. |
| 2010/0136123 | A1 | 6/2010 | Izumida et al. |
| 2011/0177141 | A1 | 7/2011 | Celeste |
| 2012/0282317 | A1 | 11/2012 | Ekstein |
| 2013/0011523 | A1 | 1/2013 | Belzowski et al. |
| 2013/0011525 | A1 | 1/2013 | Belzowski et al. |
| 2013/0011529 | A1 | 1/2013 | Belzowski et al. |
| 2013/0087144 | A1 | 4/2013 | Todd |
| 2013/0089600 | A1 | 4/2013 | Winnicki |
| 2013/0184354 | A1 | 7/2013 | Jackson et al. |
| 2015/0257407 | A1 | 9/2015 | Glazier et al. |
| 2016/0051480 | A1 | 2/2016 | Taha |
| 2016/0256411 | A1 | 9/2016 | Aung-Din |
| 2016/0296474 | A1 | 10/2016 | Romanoschi et al. |
| 2016/0354561 | A1 | 12/2016 | Mccullough |
| 2017/0050010 | A1 | 2/2017 | Mcallister et al. |
| 2017/0112188 | A1 | 4/2017 | Ostrander |
| 2017/0119660 | A1 | 5/2017 | Temtsin-Krayz et al. |
| 2017/0172977 | A1 | 6/2017 | Kleidon et al. |
| 2017/0196923 | A1 | 7/2017 | Moore |
| 2017/0245550 | A1 | 8/2017 | Freelander |

(Continued)

FOREIGN PATENT DOCUMENTS

| | | | |
|---|---|---|---|
| CA | 2984915 | A1 | 6/2017 |
| CA | 2969158 | A1 | 12/2018 |

(Continued)

OTHER PUBLICATIONS

Masek et al. (Multi-layered nanofibrous mucoadhesive films for buccal and sublingual administration of drug-delivery and vaccination nanoparticles—important step towards effective mucosal vaccines) Journal of controlled release, vol. 249, Mar. 10, 2017, pp. 183-195 (Year: 2017).*

Peshkovsky, Are Cannabinoids More Effective in Nano Form?, Sonomechanics Blog, Industrial Sonomechanics, May 28, 2016.

Fan et al., "Development of a drop-on-demand droplet generator for one-drop-fill technology", Sensors and Actuators A: Physical, 147, 2008, 649-655.

Greenberg, Cannabis Scientists Are Chasing the Perfect High, The New York Times Magazine, https://www,nytimes.com/2020/04/01/magazine/cannabis-science.html, Apr. 1, 2020.

Hadzhykanova, E. "Edible Dosage Chart: How Much Is Enough", pp. 15, Honest Mariuana.pdf at Adobe Acrobat Pro (32 bit). (Year: 2016).

(Continued)

*Primary Examiner* — Robert A Wax
*Assistant Examiner* — Kimberly Barber
(74) *Attorney, Agent, or Firm* — Gray Ice Higdon

(57) ABSTRACT

A layered edible product includes a core and at least one active layer that is supported by the core. The at least one active layer can include a respective API. The edible product is configured to be placed against a mucosal surface of the oral cavity, which causes the respective API of the at least one active layer to enter the bloodstream through the mucosal surface. The core can be ingested gastrointestinally or can be dissolvable against the mucosal surface or both. The core can include a core API, or optionally the core can be API-free.

35 Claims, 8 Drawing Sheets

(56) References Cited

U.S. PATENT DOCUMENTS

| | | | |
|---|---|---|---|
| 2017/0368021 | A1 | 12/2017 | Atkinson et al. |
| 2018/0117161 | A1 | 5/2018 | Docherty et al. |
| 2018/0140965 | A1 | 5/2018 | Flora et al. |
| 2018/0141277 | A1 | 5/2018 | Warner et al. |
| 2018/0221332 | A1 | 8/2018 | Renwick et al. |
| 2018/0297726 | A1 | 10/2018 | Ruben |
| 2019/0001087 | A1 | 1/2019 | Davidson et al. |
| 2019/0015383 | A1 | 1/2019 | Woelfel et al. |
| 2019/0022055 | A1 | 1/2019 | Siegel et al. |
| 2019/0030101 | A1 | 1/2019 | Cooper et al. |
| 2019/0073127 | A1 | 3/2019 | Ravindranath |
| 2019/0082728 | A1 | 3/2019 | Eaton |
| 2019/0116808 | A1 | 4/2019 | Tedeschi et al. |
| 2019/0192428 | A1 | 6/2019 | Goskonda et al. |
| 2019/0195852 | A1 | 6/2019 | Bryant et al. |
| 2019/0373679 | A1 | 12/2019 | Fu et al. |
| 2020/0330424 | A1 | 10/2020 | Bruun et al. |
| 2020/0352826 | A1 | 11/2020 | Warren et al. |
| 2021/0267933 | A1 | 9/2021 | Bruun et al. |

FOREIGN PATENT DOCUMENTS

| | | | |
|---|---|---|---|
| CA | 3040547 | C | 12/2021 |
| JP | 11-235164 | A | 8/1999 |
| JP | 2006-504671 | A | 8/2002 |
| JP | 2005-531330 | A | 10/2005 |
| JP | 2013-521811 | A | 6/2013 |
| JP | 2013-521812 | A | 6/2013 |
| JP | 2013-521813 | A | 6/2013 |
| JP | 2017-517295 | A | 6/2017 |
| JP | 2018-505912 | A | 3/2018 |
| JP | 2018-507262 | A | 3/2018 |
| KR | 10-2011-0088991 | A | 8/2011 |
| WO | 99/42000 | A1 | 8/1999 |
| WO | 2005/123569 | A2 | 12/2005 |
| WO | 2015/164840 | A1 | 10/2015 |
| WO | 2016/094810 | A2 | 6/2016 |
| WO | 2016/141056 | A1 | 9/2016 |
| WO | 2017/027528 | A1 | 2/2017 |
| WO | WO2018236729 | A1 * | 12/2018 |
| WO | 2019/014631 | A1 | 1/2019 |
| WO | 2019/073127 | A2 | 4/2019 |
| WO | 2022/013869 | A1 | 1/2022 |

OTHER PUBLICATIONS

Helena Miles, “Microdosing Cannabis: The Ultimate Beginne s Guide”, Wayback Machine—https://web.archive.Jrg/web/20191117102654/https://greencamp.com/microdosing, Feb. 14, 2019, pp. 1-6.

International Search Report and Written Opinion dated Jul. 29, 2020 issued in PCT/US2020/031128; 18 Pages.

Miles, Helena, “Microdosing Cannabis: The Ultimate Beginner’s Guide”. The Ultimate Beginner_s.pdf. (Year: 2019).

McKeil, Not ready to come down? How to make your high last longer, https://cannigma.com/physiology/hot-to-make-your-high-last-longer/?utm_source=USA%20Canada%20-%20West%20Coast&utm_medium=email&utm_campaign=Newsletter%2016.12.2021%20Group%203%20%28VPi6yJ%2 9&_kx=-zL7LKXrLzYFoWsw0sAGYCyQFTQ4cWfWo_b3agA9IEAr78vphArutv7JJrnpbm-n.J8JtEm, The Cannigma, Dec. 2021, 7 pages.

* cited by examiner

LAYERED EDIBLE PRODUCT FOR MULTI-STAGE DOSING OF MULTI-FUNCTION ACTIVE PHARMACEUTICAL INGREDIENTS

CROSS-REFERENCE TO RELATED APPLICATIONS

This claims priority to U.S. Patent Application Ser. No. 63/311,893 filed Feb. 18, 2022, the disclosure of which is hereby incorporated by reference as if set forth in its entirety herein.

BACKGROUND

Conventional *cannabis* edible products include *cannabis* active pharmaceutical ingredients (API), which include one or more cannabinoids (primarily cannabidiol (CBD) and tetrahydrocannabinol (THC), terpenes, and flavonoids. The edible products are typically designed to be orally consumed to undergo mastication and swallowing, followed by gastrointestinal digestion. However, it has been found that only a small percentage of a *cannabis* active ingredient such as THC that is orally ingested ends up absorbed into the bloodstream, and only a fraction of that absorbed *cannabis* reaches the brain. It has been found in some instances that as low as 20% of *cannabis* in the edible is absorbed by the body, and as low as 10% of the *cannabis* of the edible reaches the brain. The actual amount that is absorbed by the body can be dependent on the volume and type of food that has been recently consumed. While food products high in fat content can cause higher levels of *cannabis* to reach the liver, this does not necessarily equate to the higher levels of *cannabis* reaching the brain. Therefore, even though *cannabis* potency can be increased in the liver, overall a comparatively small and unpredictable dosage of the gastrointestinally digested *cannabis* contributes to a desired therapeutic effect.

Further, the API is typically incorporated in the edible product prior to cooking. For instance, the API is often added to the batter or other ingredient mixture that is then baked to produce the edible product. However, the high temperatures associated with cooking can evaporate terpenes and thermally degrade additives such as vitamins or supplements, thus harming the desired therapeutic profile of the edible product. Moreover, the healthful acidic forms of CBD and THC or other acidic cannabinoids are partially or completely eliminated during the cooking process.

What is therefore needed is an improved API-containing edible product, and an improved method of ingesting the improved API-containing edible product.

SUMMARY

In accordance with certain aspects of the present disclosure, a layered edible product can include a core and at least one active layer disposed over the core. The core can include a core API, and the at least one active layer can include an inner API. The at least one active layer can be dissolvable against a sublingual mucosa and a buccal mucosa.

In accordance with other aspects of the present disclosure, the at least one active layer can be intentionally dissolvable against a sublingual mucosa and a buccal mucosa to achieve fast onset effects, followed by a longer-duration set of independent effects determined by the core API.

DETAILED DESCRIPTION

Figure 1A:
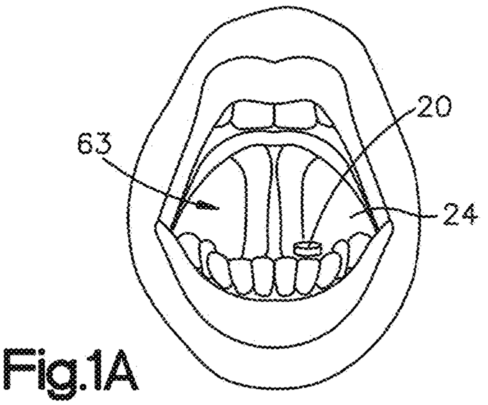
FIG. 1A is a perspective view of a layered edible being dissolved against a sublingual mucosa.

Disclosed are layered edible products that contain a core and at least one active layer. The at least one active layer including at least one active pharmaceutical ingredient (API) can be configured to undergo transmucosal absorption into the bloodstream through a mucosa in the oral cavity, such as the sublingual mucosa or the buccal mucosa. Thus, the API of the at least one active layer can enter the bloodstream and provide its intended therapeutic effect with little delay. The core can be configured to be chewed and swallowed. Accordingly, when the core includes at least one core API, the therapeutic effect of the core API is delayed with respect to the API of the at least one active layer. Thus, the user experiences the therapeutic effect of the core API after experiencing the therapeutic effect of the API of the at least one active layer. The API of the at least one layer can be configured to provide its therapeutic effect for a duration sufficient to last substantially until the core API delivers its therapeutic effect. Alternatively, the API of the at least one layer can be configured such that its therapeutic effect terminates prior to the delivery of the therapeutic effect of the core API. Alternatively still, the API of the at least one layer can be configured such that its therapeutic effect has a sufficient duration so as to overlap with the therapeutic effect of the core API. As will be appreciated from the description below, the at least one active layer can include a single active layer, inner and outer active layers, or any number of active layers as desired. The layered edible products allow for an end user to select a layered edible product of their choosing for consumption among the kit of available layered edible products that best corresponds to the desired therapeutic effects of the end user, which may be best optimized by selecting the layered edible product having the desired API chemistries of the inner layer, the core (if present), and the outer layer (if present) along with their respective desired time durations. The APIs of the outer layer (if present) and the inner layer can offer therapeutic effects for relatively short durations that can be optimized based on consumer needs, such as near-term or immediate calmness or other therapeutic effect as desired, whereas the core can provide a longer duration of therapeutic effect, and can be optimized for quality of overnight sleep or other therapeutic effect as desired.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this document and the title are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods, and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single apparatus is described herein, it will be readily apparent that more than one apparatus may be used in place of a single apparatus. Similarly, where more than one apparatus is described herein, it will be readily apparent that a single apparatus or article may be used in place of the more than one apparatus, and vice versa. Thus, a description herein using the singular "a" applies with full force and effect to "at least one" and "a plurality" unless otherwise indicated. Further, a description herein using the plural term "a plurality" applies with equal force and effect to the singular "a" and "at least one" unless otherwise indicated.

The functionality or the features of an apparatus may be alternatively embodied by one or more other apparatus that are not explicitly described as having such functionality or features. Thus, other aspects need not include the apparatus itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions should be understood as representing modules, segments, or portions of methodologies which can include one or more steps for implementing a portion or an entirety of a process. Alternate implementations are included within the scope of various aspects in which, for example, functions may be executed out of order from that shown or discussed, including substantially concurrently or in reverse order, depending on the functionality involved, as would be understood by those having ordinary skill in the art.

Figure 1B:
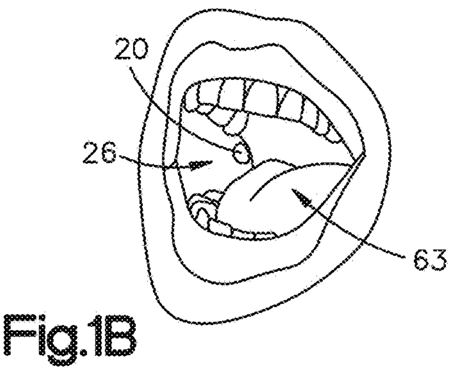
FIG. 1B is a perspective view of a layered edible being dissolved against a buccal mucosa.

Referring now to FIGS. 1A-1B, a layered edible product 20 can include at least one active layer 22 that contains at least one active pharmaceutical ingredient (API). The at least one active layer 22 can be dissolvable by saliva against a sublingual mucosa 24 shown in FIG. 1A so as to deliver the API directly into the bloodstream. The at least one active layer 22 can also be dissolvable by saliva against a buccal mucosa 26 shown in FIG. 1B so as to deliver the API through the mucosa and directly into the bloodstream. The at least one active layer 22 can include a single active layer, inner and outer active layers, or any number of active layers as desired. Thus, the user can decide whether to place the layered edible product 20 against the sublingual mucosa 24 or the buccal mucosa 26. Regardless of whether the product 20 is placed against the sublingual mucosa 24 or the buccal mucosa 26, the bioavailability of the API is greater than that through gastrointestinal digestion. Further, the API reaches the brain far more quickly as compared to gastrointestinal digestion. Thus, ingestion across each mucosal membrane can allow the API to have a greater therapeutic effect in a shorter period of time compared to gastrointestinal digestion.

As will be described in more detail below, the layered edible product 20 can further include a core that can be chewed, swallowed, and therefore subject to gastrointestinal digestion. The gastrointestinal digestion can subject the user to time delayed therapeutic effects of the core API compared to the mucosal ingestion of the at least one active layer 22. Thus, the API from the at least one active layer 22 can provide more immediate therapeutic effects, and the core API of the core can provide therapeutic effects temporally delayed with respect to the effects of the API from the at least one active layer 22. Further, as will be described in more detail below, the API of the at least one layer and the core API can have different constituent components or different ratios of the same constituent components as desired, depending on the desired effects.

The layered edible product 20 in accordance with one example will now be described with reference to FIGS. 2A-2B. In particular, in one example the layered edible product 20 can define a stacked edible body 54 having a core 30 that defines a base of the edible product 20. The core 30 can be defined by any suitable edible food product as desired. Edible food products can include, by way of example and not limitation, hard candy, chocolates, brownies, cookies, soft candies such as gummy candy, savories such as trail mix bars or dried meat pieces, and the like. Thus, in some examples, the edible food products can be cooked food product. In some specific examples, the edible food products can be baked food product. Edible food product can be bite sized, such as M&M candy, gummy candies, chocolate kisses, or the like, or can be designed to require more than one bite for full consumption, such as a cookie or large brownie. It should be appreciated in some examples, the edible food product can include a plurality of ingredients that can be mixed and baked or otherwise cooked during preparation.

In some examples, the core 30 can deliberately not include an API, referred to herein as inert. In other examples, the core 30 can include a core API to define an active core. In some examples, the core API can include one or more of a core non-psychoactive cannabinoid, a core psychoactive cannabinoid, a core flavonoid, and a core terpene. The core 30 can be of any composition as desired. In some examples, the core API can be incorporated into the core 30 during preparation of the food product. For instance, the core API can be added to the mixture prior to cooking. Alternatively, the core API can be added to the edible food product after cooking but prior to final preparation of the food product. For instance, it may be desirable to add one or more auxiliary edible products to the prepared edible product, either before or after delivering the core API to the edible food product. Examples include adding icing to a cookie, or frosting to a brownie or cake, or the like. However, in these examples, the cookie and brownie can have been fully cooked or otherwise prepared prior to adding the core API. In still other examples, the core API can be added to the core 30 after preparation of the food product. In other examples, the edible food product can be a dehydrated food product, such as dried fruit or jerky. In other examples, the edible food product can be freeze dried. In still other examples, the edible food product can be a raw food product, such as a nut or fruit. In some examples, the nut has been cooked, such as roasted. In other examples, the nut can be raw. In some instances, the nut can be prepared with salt, sugar, honey, or any suitable alternative ingredient. Thus, the nut can be candied. Similarly, the fruit can be a raw fruit. In other examples, the fruit can be dried. In still other examples, the fruit can be prepared with salt, sugar, honey, or any suitable alternative ingredient, and can thus be candied. In other examples, the core 30 can be a commercially available edible product that contains a respective core API. Thus, the core 30 can be procured, and the at least one active layer can be applied to the core 30 in any suitable manner as described herein. Alternatively, the core 30 can be configured as an edible non-food product, such as a product that is not designed to be consumed but can be safely consumed with no or a negligible nutritional effect. Alternatively still, the core 30 can be configured as any other inedible substrate, such as a tongue depressor.

The core 30 can define at least one or more core external surfaces 33 that in one example can include a core inner surface 32 and a core outer surface 34 that is opposite the core inner surface 32 along a longitudinal direction L. The core 30 can have define any suitable shape as desired. For instance, either or both of the core inner surface 32 and the core outer surface 34 can be substantially planar, curved, or can assume any suitable alternative shape as desired. The core 30 can further define at least one core side 36 that extends from the core inner surface 32 to the core outer surface 34. The at least one core side 36 can include a singular side 36 that substantially defines a cylinder. Alternatively, the at least one core side 36 can be square or rectangular or ellipsoidal, or can define any suitable alternative shape in cross section as desired. In still other examples, the core 30 can be devoid of the core side 36, for instance when the core 30 is round as described below with reference to FIGS. 3A-3C. In this regard, it should be appreciated that the core 30 can define any regular or irregular shape as desired.

The term "substantially," "approximately," and derivatives thereof, and words of similar import, when used to described sizes, shapes, spatial relationships, distances, directions, expansion, and other similar parameters includes the stated parameter in addition to a range up to 20% more and up to 20% less than the stated parameter, including up to 10% more and up to 10% less than the stated parameter, including up to 5% more and up to 5% less than the stated parameter, including up to 3% more and up to 3% less than the stated parameter, including up to 1% more and up to 1% less than the stated parameter.

The layered edible product 20 can further include at least one active layer 22 that is disposed over the core. Each at least one active layer 22 can include an API as will be described in more detail below. In one configuration, at least one active layer 22 can include an inner active layer 40 and an outer active layer 42. The inner and outer active layers 40 and 42 can be arranged such that the inner active layer 40 is disposed between the core 30 and the outer active layer 42 along the longitudinal direction L. The at least one active layer 22 can include any number of active layers as desired, including one active layer or more than one active layer. The inner active layer 40 can define an inner surface 44, an outer surface 46 that is opposite the inner surface 44 along the longitudinal direction L, and a first at least one side 45 that extends from the inner surface 44 to the outer surface 46. The first at least one side 45 can include a singular side that substantially defines a cylinder. Alternatively, the first at least one side 45 can be square or rectangular or ellipsoidal, or can define any suitable alternative shape in cross section as desired. Alternatively, the inner active layer 40 can be devoid of the at least one side 45, for instance when the inner active layer 40 is round as described below with reference to FIGS. 3A-3C. In this regard, it should be appreciated that the inner active layer 40 can define any regular or irregular shape as desired. The outer surface 46 can face a direction toward the outer active layer 42. The inner surface 44 can face a direction away from the outer active layer 42, and thus can face the core 30 and in particular can face the core outer surface 34. In one example, the inner surface 44 can be disposed on the core outer surface 34. The outer core surface 34 can face the inner active layer 40, and the core inner surface 32 can face away from the inner active layer 40.

The outer active layer 42 can define an inner surface 48, an outer surface 50 that is opposite the inner surface 48 along the longitudinal direction L, and a second at least one second side 49 that extends from the inner surface 48 to the outer surface 50. The second at least one side 49 can include a singular side that substantially defines a cylinder. Alternatively, the second at least one side 49 can be square or rectangular or ellipsoidal, or can define any suitable alternative shape in cross section as desired. In still other examples, the outer active layer 42 can be devoid of the second at least one side 49, for instance when the outer active layer 40 is round as described below with reference to FIGS. 3A-3C. The inner surface 48 can face the inner active layer 40, and in particular can face the outer surface 46. In one example, the at least one core side 36, the first at least one side 45, and the second at least one side 49 can be substantially aligned with each other along the longitudinal direction L. Alternatively, one or more of the at least one core side 36, the first at least one side 45, and the second at least one side 49 can be out of alignment with one or more up to all of the others of the at least one core side 36, the first at least one side 45, and the second at least one side 49 along the longitudinal direction L.

The layered edible product 20 can include at least one partition layer 52 disposed between adjacent active layers of the at least one active layer 22. Thus, a partition layer 52 can be disposed between the inner and outer active layers 40 and 42. The partition layer 52 can be inert, and thus devoid of API. The partition layer 52 can be disposed between an entirety of the outer surface 46 of the inner active layer 40 and the inner surface 48 of the outer active layer 42. In particular, the partition layer 52 can define an inner partition surface 53, an outer partition surface 56 that is opposite the inner partition surface 53 along the longitudinal direction L, and at least one partition side 58 that extends from the inner partition surface 53 to the outer partition surface 56. The at least one partition side 58 can be in substantial alignment with the first and second at least one sides 45 and 49 along the longitudinal direction L. The partition layer 52 can be dissolvable against mucosa, including the buccal mucosa and sublingual mucosa as described above. In one aspect, the partition layer 52 can assist in adhesion of the outer active layer 42 to the inner active layer 40. The partition layer 52 can also provide a taste separation between the outer active layer 42 and the inner active layer 40 when the active layers have different taste profiles.

The partition layer 52 can also provide time a delay between the absorption of the outer active layer 42 into the bloodstream and the absorption of the inner active layer 40 into the bloodstream. In particular, the partition layer 52 can have a thickness that is sufficient to separate the inner active layer 40 from the outer active layer 42 such that at least a majority up to a substantial entirety of the inner active layer 40 can be dissolved in the oral cavity before the inner active layer 40 is dissolved in the oral cavity. Thus, when a partition layer 52 is disposed between two different API-containing structures (which can be an active layer or the core 30), a majority up to a substantial entirety of an outer one of the two different API-containing structures can be absorbed in the oral cavity before the inner one of the two different API-containing structures is ingested, either against a mucosa of the oral cavity or masticated and swallowed. As a result, when the API of the inner active layer 40 (also referred to herein as an inner API) and the API of the outer active layer 42 (also referred to herein as an outer API) have different constituent components as described in more detail below, the partition layer 52 prevents the ingestion of the inner API until at least a majority up to a substantial entirety of the outer API has been ingested. The partition layer 52 can also reduce or prevent unwanted chemical interference between non-API components of the separated layers, such as solvents or adherents. The thicknesses of the inner active layer 40 and the outer active layer 42 can each be in the range of sub-nanometers to nanometers up to millimeters, as desired. The thickness of the core 30 can be greater than that of the inner and outer active layers 40 and 42, so as to provide structural rigidity for the layered edible product 20.

While the inner surface 44 can be disposed directly on the core outer surface 34 in one example, the layered edible product 20 can alternatively include a partition layer 52 that is disposed between the inner surface 44 and the core outer surface 34 in the manner described above with respect to the inner active layer 40 and the outer active layer 42. The core 30, the at least one active layer 22, and the at least one partition layer 52, and any other layers to be consumed, can combine so as to define an edible body 54 that can be covered or surrounded by a wrapper 60. Thus, the layered edible product 20 can include the edible body 54 and the wrapper 60 that can cover or surround the edible body 54. In one example, the wrapper 60 can fully encapsulate the edible body 54. In other examples, the wrapper 60 can cover at least an outermost surface 55 of the edible body 54. For instance, the wrapper 60 can cover all but the core 30, and can be adhered to the core 30 or otherwise secured to the core 30 as desired. The outermost surface 55 of the edible body 54 can be defined by the outer active layer 42 or other outermost active layer of the at least one active layer 22. The wrapper 60 can be dissolvable against the sublingual mucosa and the buccal mucosa in some examples. In other examples, the wrapper 60 is inedible and designed to be manually removed from the edible body 54 without being ingested prior to ingestion of the edible body 54. In still other examples, the layered edible product 20 can include a first wrapper layer that is dissolvable against the sublingual mucosa and the buccal mucosa, and a second wrapper layer that is inedible and designed to be manually removed. The wrapper 60 can be inert and thus devoid of API. In some applications, the wrapper 60 can be configured to retain volatile components such as terpenes or flavonoids in the layered edible product 20 until the wrapper 60 is removed and the edible body 54 is placed in the mouth. The wrapper 60, when dissolvable, can be applied in any suitable manner known by those having ordinary skill in the art of food science, including but not limited to powder deposition, baths, droplets, sprays, and the like. In still other examples, the layered edible product 20 can be devoid of the wrapper 60. For instance, a plurality of layered edible products 20 can be disposed in a common package.

Figure 2A:
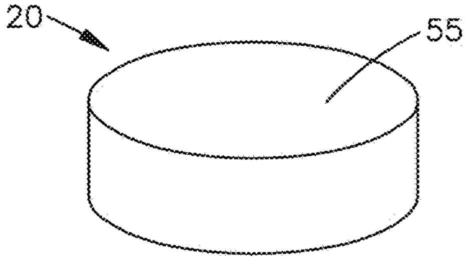
FIG. 2A is a perspective view of a layered edible product constructed in one example having a substantially planar geometry.
Figure 2B:
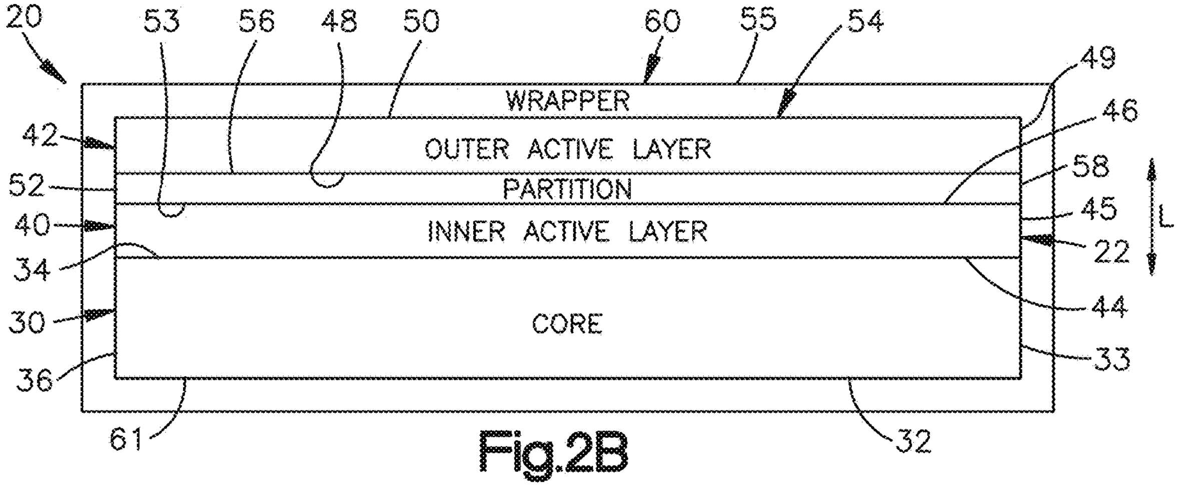
FIG. 2B is a schematic sectional side elevation view of the layered edible product of FIG. 2A showing a core, an inner active layer that includes an inner at least one API disposed over the core, and an outer active layer that is disposed over the inner active layer and includes an outer at least one API, a partition layer disposed between the inner and outer active layers, and a wrapper that covers the outer active layer.
Figure 2C:
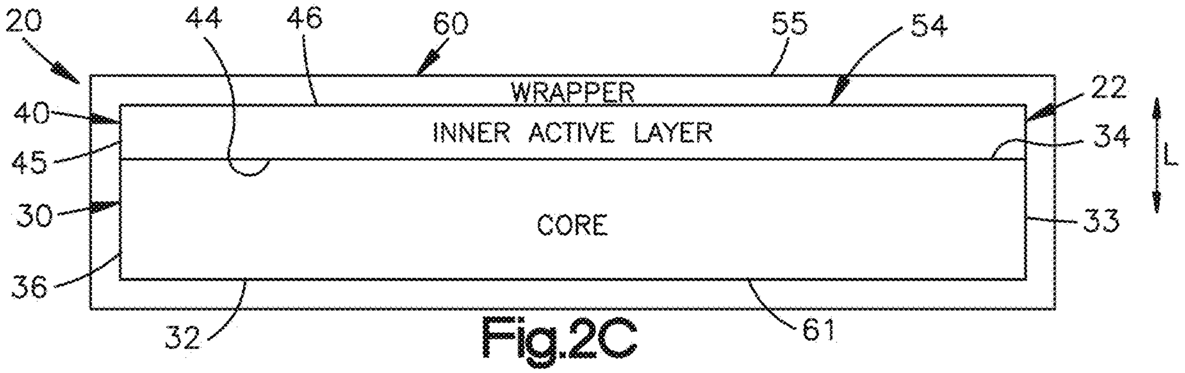
FIG. 2C is a schematic side elevation view of a layered edible product similar to FIG. 2B, but whereby an active layer is disposed directly on the core.

Referring now to FIG. 2C, and as described above, the layered edible product 20 can include any number of active layers as desired. For instance, the at least one active layer 22 of the edible body 54 can include only a single active layer that is defined by the inner active layer 40. The inner surface 44 can face the core 30, and in particular can face the core outer surface 34. In one example, the inner surface 44 can be disposed on the core outer surface 34. In another example, a partition layer 52 (see FIG. 2B) can be disposed between the inner surface 44 and the core outer surface 34. The outermost surface 55 of the edible body 54 can thus be defined by the inner active layer 40, and in particular by the outer surface 46. The wrapper 60 can thus cover at least the outer surface 46. It should be appreciated in the example of FIG. 2C that the inner active layer 40 defines both an outermost active layer of the edible body 54 and an innermost active layer of the edible body 54 such that no active layer is disposed between the inner active layer 40 and the core 30. Otherwise stated, the inner active layer 40 can define the sole active layer of the edible body 54. In the example of FIG. 2B, the inner active layer 40 defines the innermost active layer of the layered edible product 20 and the outer active layer 42 defines the outermost active layer of the layered edible product 20.

As shown in FIGS. 2A-2C, the core inner surface 32 can define an innermost surface 61 of the edible body 54. In some examples, the wrapper 60 covers the outermost surface 55 but does not cover the innermost surface 61. Thus, the core inner surface can be uncovered by any other portion of the edible body 54. As a result, the core inner surface 32 can also define an innermost surface of the layered edible product 20, and the wrapper 60 defines an outermost surface of the layered edible product 20. In other examples, the wrapper 60 can surround an entirety of the edible body 48 so as to define the outermost and innermost surfaces of the layered edible product 20.

It should be appreciated that while the core 30 and the at least one active layer 22 can define a stacked edible body 54 whereby the at least one active layer is stacked onto one surface of the core 30 but not an opposed surface of the core 30 as described above, the core 30 and the at least one active layer 22 can define any suitable geometrical configuration as desired. For instance, referring now to FIGS. 3A-3C, the edible body 54 can define an encapsulation body 57. Further, the edible body 54 can be substantially concentrically arranged. That is, the core 30, the at least one active layer 22, and the at least one partition layer 52 can be substantially concentrically arranged with each other.

As shown, the inner active layer 40 can at least partially surround or encapsulate the core 30. In particular, the inner surface 44 can face toward the at least one core external surface 33. For instance, the inner surface 44 can face toward the core outer surface 34. Depending on the shape of the core 30, the inner surface 44 can further face each at least one core side 36 if present. Thus, the inner surface 44 of the inner active layer 40 can face toward all external surfaces 33 of the core 30. In some examples, the inner active layer 40 can entirely surround the core 30. In other examples, the inner active layer 40 can include one or more openings as desired that extend from the outer surface 46 to the inner surface 44. Either way, it can be said that the inner active layer 40 substantially encapsulates the core 30. Because the inner active layer 40 can extend continuously about the core 30, the inner active layer 40 can be devoid of the first at least one side 45 described above with respect to FIGS. 2A-2C.

In one example, the inner surface 44 can contact the at least one core external surface 33. Thus, the inner active layer 40 can conform to the shape of the external surface 33 of the core 30. In other examples, the edible body 54 can include a partition layer 52, of the type described herein, that is disposed between the core 30 and the inner active layer 40. Whether the inner active layer 40 directly contacts the core 30 or a partition layer that is disposed between the inner active layer 40 and the core 30, it can be said that the inner active layer 40 substantially encapsulates the core 30. Further, because the partition layer, if present, can conform to the shape of the external surface 33 of the core 30, and the inner active layer 40 can conform to the shape of the partition layer, the inner active layer 40 can conform to the shape of the external surface of the core 30 when a partition layer is present. Further, when the partition layer is disposed between the core 30 and the inner active layer 40, the inner active layer 30 also can be said to substantially encapsulate each of the partition layer and the core 30.

The at least one core external surface 33 can define any suitable size and shape as desired, such as an ovoid, a sphere, a cylinder, or any suitable alternative shape as desired. Thus, the core inner surface 32 (see FIGS. 2B-2C), the core outer surface 34, and the core side 36 can be continuous with each other, or can define respective intersections as desired. In other examples, the core 30 can be devoid of the core side 36. The thickness of the inner active layer 40 from the inner surface 44 to the outer surface 46 can be substantially consistent along an entirety of the inner active layer 40. Alternatively, if desired, portions of the inner active layer 40 can be thicker or thinner than other portions of the inner active layer 40.

Figure 3A:
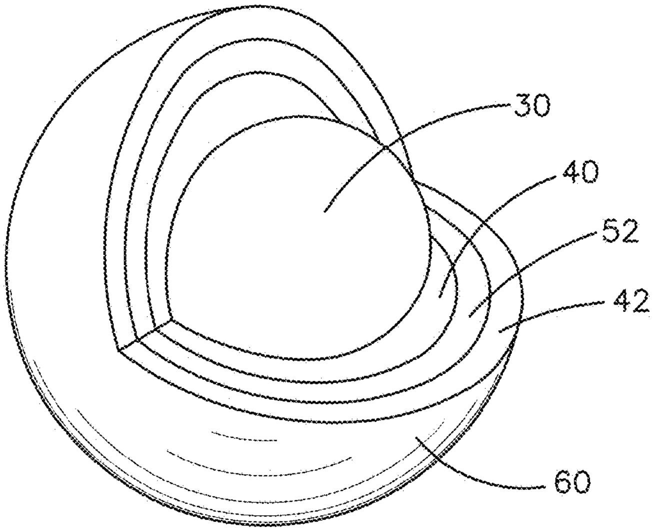
FIG. 3A is a schematic sectional side elevation view of a spherical layered edible product having a substantially encapsulated geometry in accordance with another example, with a portion cut away to show a core, an inner active layer disposed about the core, a partition layer disposed about the inner active layer, an outer active layer disposed about the inner active layer, and a wrapper is disposed about the outer active layer.
Figure 3B:
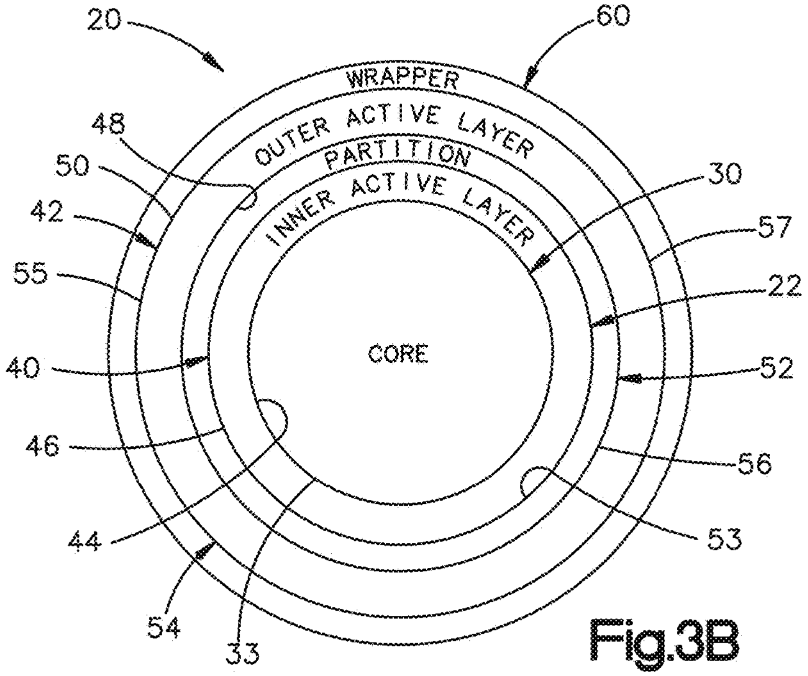
FIG. 3B is a schematic sectional side elevation view of the edible product shown in FIG. 3A.

With continuing reference to FIGS. 3A-3B, the outer active layer 42 can at least partially surround or encapsulate the inner active layer 40. In particular, the inner surface 48 can face toward the outer surface 46. Thus, the inner surface 48 of the outer active layer 42 can face toward all external surfaces of the core 30 and the inner active layer 40. In some examples, the outer active layer 42 can entirely surround the inner active layer 40. In other examples, the outer active layer 42 can include one or more openings as desired that extend from the outer surface 50 to the inner surface 48. Either way, it can be said that the outer active layer 42 substantially encapsulates the inner active layer 40. Because the outer active layer 42 can extend continuously about the inner active layer 40, the outer active layer 42 can be devoid of the second at least one side 49 described above with respect to FIG. 2B.

In one example, the edible body 54 can include a partition layer 52, of the type described herein, that is disposed between the inner active layer 40 and the outer active layer 42. Thus, the partition layer 52 can contact and extend about the outer surface 46. Thus, the partition layer 52 can substantially encapsulate the inner active layer 40. The outer active layer 42 can contact and extend about the partition layer 52. Thus, the outer active layer 42 can substantially encapsulate the partition layer 52. It can also be said that the outer active layer 42 substantially encapsulates the inner active layer 40 and the core 30. The partition layer 52 can conform to the shape of the outer surface 46 of the inner active layer 40. The outer active layer 42 can conform to the shape of the partition layer 52, and thus of the inner active layer 40, and thus of the core 30. Accordingly, the core 30, all partition layers 52, and each at least one active layer 22 can have the same shape.

In other examples, edible body 54 can be devoid of a partition layer 52 between the inner and outer active layers 40 and 42, such that the inner surface 48 can contact the outer surface 46. When there is no partition layer between the inner and outer active layers 40 and 42, the outer active layer 42 can again be said to conform to the shape of the outer surface 46 of the inner active layer 40. Whether the outer active layer 42 directly contacts the inner active layer 40 or the partition layer 52 is disposed between the inner active layer 40 and the outer active layer 42, it can be said that the outer active layer 42 substantially encapsulates the inner active layer 40 and the core 30. Further, all outer surfaces of the inner active layer 40 face toward the outer active layer 42.

As described above, the edible body 54, including the core 30, the at least one active layer 22, and any partition layers 52 can define any suitable shape. In one example, the shape can be substantially spherical, and thus does not include discrete sides that extend from respective inner surfaces to outer surfaces. In another example, the shape can be substantially ellipsoidal. In still other examples, the shape can be substantially cylindrical or disc shaped. In other examples, the shape can be nonregular, that is, not exhibiting perfect symmetry about any axis. Thus, the core and the at least one active layer can include the respective sides that extend from the respective inner surfaces to the respective outer surfaces as described above.

As described above, the layered edible product 20 can include a wrapper 60 that can surround the edible body 54. In particular, the wrapper 60 can cover or surround an entirety of the outermost surface 55 of the edible body 54. The outermost surface 55 can be fully defined by an outermost one of the at least one active layer 22. In one example, the wrapper 60 can surround the outer active layer 42 that defines the outermost one of the at least one active layer 22. As described above, the wrapper 60 can be dissolvable against the sublingual mucosa and the buccal mucosa in some examples. In other examples, the wrapper 60 is inedible and designed to be manually removed from the edible body 54 prior to ingestion of the edible body 54. In still other examples, the layered edible product 20 can include a first wrapper layer that is dissolvable against the sublingual mucosa and the buccal mucosa, and a second wrapper layer that is exterior with respect to the first wrapper layer and is inedible and designed to be manually removed. The wrapper 60 can be inert and thus devoid of API.

Figure 3C:
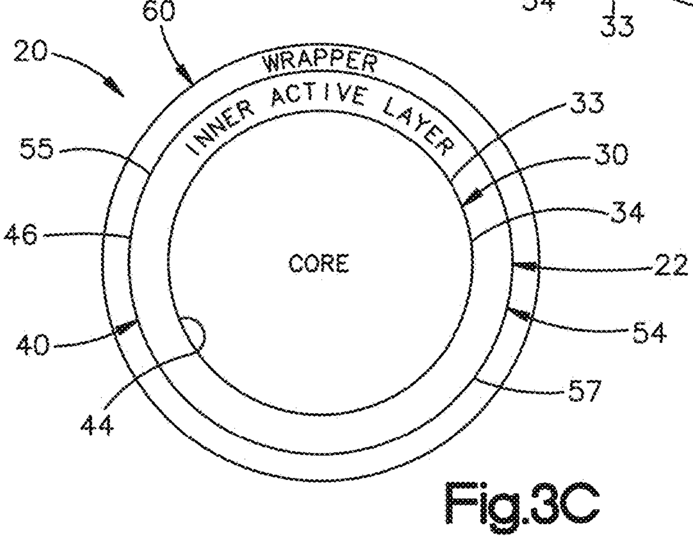
FIG. 3C is a schematic sectional side elevation view of a layered edible similar to FIG. 3B, but wherein the inner active layer is disposed directly on the core.

Referring now to FIG. 3C, and as described above, the encapsulation body 57 can include any number of active layers as desired. For instance, the at least one active layer 22 of the encapsulation body 57 can include only a single active layer that is defined by the inner active layer 40. The inner surface 44 can substantially encapsulate the core 30. In particular, the inner surface 44 can face the core outer surface 34. In one example, the inner surface 44 can be disposed on the core outer surface 34. In another example, a partition layer 52 (see FIG. 3B) can be disposed between the inner surface 44 and the core outer surface 34. The outermost surface 55 of the edible body 54 can thus be fully defined by the inner active layer 40, and in particular by the outer surface 46. The wrapper 60 can thus cover the outer surface 46. It should be appreciated in the example of FIG. 3C that the inner active layer 40 defines both an outermost active layer of the encapsulation body 57 and an innermost active layer of the encapsulation body 57, such that no active layer is disposed between the inner active layer 40 and the core 30. Otherwise stated, the inner active layer 40 is the sole active layer of the encapsulation body 57. In the example of FIG. 3B, the outer active layer 42 defines the outermost surface 55 of the edible body 54.

In all embodiments described above with respect to FIGS. 1-3C, each of the core 30, and each at least one active layer 22 can include at least one active pharmaceutical ingredient (API). The at least one API can include *cannabis*, including acidic, neutral, and/or emulsified forms of *cannabis*, or other non-*cannabis* substances. The term "*cannabis*" as used herein refers to any extract from a marijuana plant or hemp plant, such as CBD, THC, any alternative cannabinoid, or any chemically synthesized *cannabis* substance, alone or in combination with any one or more of a flavonoid or terpene. The terpenes and/or flavonoids can be an extract that is extracted from *cannabis* or hemp, or could be provided as pure substances acquired or synthesized commercially from other sources. The extract can be in its pure form or can be processed as desired, including, as example, emulsified forms of *cannabis* fluids. The cannabinoids can be provided as neutral cannabinoid forms or acidic cannabinoid forms as desired. The API can be provided in liquid form or any suitable alternative form as desired. Further, the API can be provided in a form that is composed of microdroplets or nanodroplets, each of which is substantially encapsulated by an encapsulation of film of molecules that can be hydrophilic and/or lipophilic as desired. The encapsulation can be constructed as any one of liposomes, emulsions, solid-lipid nanoparticles, self-nano-emulsifying drug delivery system (SNEDDS) particles, and the like. While this disclosure provides for the addition of at least one *cannabis* to an edible or inedible substrate that defines the core 30, and thus *cannabis* is contemplated as a market for the final product, applications of the systems and methods disclosed herein are possible and envisioned that do not involve *cannabis*, including (but not limited to) other APIs. For instance, applications of the edible product and methods disclosed herein are possible and envisioned to include APIs including one or more of a cannabinoid, any alternative one or more over-the-counter (OTC) or prescription drugs including those that provide one or both of a health benefit or recreational drug experience, otherwise controlled ingestible materials, and herbal medicines, supplements, and the like. Thus, reference herein to an API can include any one or more up to all of the following: *cannabis*, and *cannabis* plant-derived compounds or synthetically-produced compounds, including one or more cannabinoids in either natural oily forms or emulsified forms, one or more over-the-counter drugs, one or more prescription drugs, one or more flavonoids, one or more terpenes, and one or more herbal medicines or supplements. Reference herein to an API can further include any one or more active ingredients having a medicinal benefit, including prescription medications and over-the-counter medications, and further including vitamins, nutritional and longevity supplements, and nootropics or so-called "smart drugs" as desired. Reference herein to an active pharmaceutical ingredient can alternatively or additionally include one or more up to all of the following: psychedelic or hallucinogenic ingredients such as psilocybin and psilocyn, and synthetic opioids can replace the more dangerous ingredients such as fentanyl, it should be appreciated that the API can alternatively or additionally include fentanyl, recognizing the accurate dosage of the type described herein can be of importance when administering an API that can have severe consequences when inaccurate dosages are administered. Similarly, reference to one or more of the active pharmaceutical ingredients identified above can apply equally to any other of the active pharmaceutical ingredients identified above. According to an aspect of the present disclosure, a method of delivering a *cannabis* or conventional drug may also be used to deliver homeopathic remedies, herbal supplements, with flavors odors, and so forth to an edible substrate. The resulting edible substrate can be referred to as a "nutraceutical," as its definition is "a food containing health-giving additives or having medicinal benefit."

The at least one API of the core 30 can be referred to as core API. The at least one API of the inner active layer 40 can be referred to as inner API. The at least one API of the outer active layer 42 can be referred to as an outer API. The inner API, the outer API, and the core API can be different from each other. In one example, the difference can be a difference in the chemistry of the constituent components, or can be a difference in the concentration of one or more of the constituent components. That is, the inner API can include at least one constituent component that is not included in the core API and the outer API. Alternatively or additionally, the core API can include at least one constituent component that is not included in the inner API and the outer API. Alternatively or additionally still, the outer API can include at least one constituent component that is not included in the inner API and the core API. The constituent component can be a constituent component of the *cannabis* group. Alternatively, the constituent component can be a prescription or over-the-counter drug or therapeutic product. In one example, the one of inner API, the outer API, or the core API can include a high concentration of terpenes or terpenes and THC, while another of the inner API, the outer API, and the core API can have high concentrations of acidic and/or neutral forms of THC and CBD, while another of the inner API, the outer API, and the core API can include high concentrations of other API components. It should be appreciated that all permutations of cannabinoids, terpenes, flavonoids, and other API constituent components are contemplated.

The constituent components of the core API, the inner API, and the outer API (when the edible body 54 includes the outer active layer 42) that are in common can be present in different proportions. In another example, the core API, the inner API, and the outer API (when the edible body 54 includes the outer active layer 42) can have the same constituent components but in different proportions. As one example, ingestion of THC can provide a psychedelic high, and ingestion of CBD can provide a calming effect. Thus, when it is desired to provide a psychedelic high, the at least one API can include a high ratio of THC with respect to CBD, or can include no CBD. When it is desired to provide a calming effect, the at least one API can include a high ratio of CBD with respect to THC, or can include no THC. Accordingly, when it is desired to provide a more immediate psychedelic high and a delayed calming effect, at least one of the active layers can have a high amount of THC with respect to CBD. When it is desired to provide a delayed calming effect, the core 30 can include a high amount of CBD with respect to THC. Conversely, if it is desired to provide an immediate calming effect, at least one of the active layers can have a high amount of CBD with respect to THC. If it is desired to provide a delayed psychedelic effect, the core can include a high amount of THC with respect to CBD.

In another example, the core API, the inner API, and the outer API (when the edible body 54 includes the outer active layer 42) can have different sensory profile, which can be defined by either or both of a flavor profile and an aroma profile. For instance, the core API can have a different sensory profile than each of the least one inner API and the at least one outer API. Further, the inner API can have a different sensory profile than each of the least one core API and the outer API. Further, still, the outer API can have a different sensory profile than each of the least one core API and the inner API. The different sensory profiles can be defined by different flavonoids and/or terpenes or the absence thereof.

Referring now to FIGS. 1-3C generally, during use the user can remove the wrapper 60 if the wrapper 60 is present and not configured for ingestion, and the edible body 54 can be placed in the oral cavity 63 against a select mucosa. The select mucosa can be defined by the sublingual mucosa 24 or the buccal mucosa 26. If the wrapper 60 is configured for ingestion, the user can place the layered edible product 20 in the oral cavity 63 against the select mucosa. The select mucosa can dissolve the wrapper 60, such that the edible body 54 remains in the oral cavity 63 against the sublingual mucosa 24. When the edible body 54 is against the select mucosa, the outermost active layer of the at least one active layer 22 is disposed against the select mucosa and is configured to dissolve against the mucosa. Accordingly, the at least one API of the outermost active layer can undergo transmucosal absorption, and thus can be delivered through the mucosa directly to the bloodstream. Once the outermost active layer has been dissolved, a sequentially inward active layer, if present, is then exposed to the select mucosa. In one example, the outermost active layer can be defined by the outer active layer 42 as shown in FIGS. 2B and 3B. In another example, the outermost active layer can be defined by the inner active layer shown in FIGS. 2C and 3C. In still other examples, the outermost active layer can be defined by a third, fourth, or other numbered active layer, depending on the number of active layers of the at least one active layer 22.

Once the outermost active layer has dissolved against the mucosa, the sequentially inner active layers can be dissolved in-turn against the mucosa until the innermost active layer has dissolved against the mucosa. The innermost active layer can be defined by the inner active layer 40 as shown in FIGS. 2A-3C. It should be appreciated that any inert partition layers 52 that are disposed between respective inner and outer adjacent active layers (such as the inner and outer active layers 40 and 42 are also dissolved. For instance, the respective outer active layer can be dissolved against the mucosa, the partition layer 52 can then be dissolved against the mucosa, and the respective inner active layer can then be dissolved against the mucosa. The partition layer 52 can help ensure that the respective outer active layer is fully or close to fully dissolved prior to exposure of the respective inner active layer is placed against the mucosa. For instance, it is recognized that certain regions of the outer active layer 42 can dissolve against the mucosa at a faster rate than other regions of the outer active layer 42. Thus, the partition layer 52 that is aligned with the certain regions can be exposed while the other regions of the outer active layer 42 are dissolving against the mucosa. Once the partition layer 52 has been dissolved, the inner active layer 40 is then exposed to the mucosa and can be dissolved against the mucosa. Thus, the inner at least one API can be absorbed through the mucosa into the bloodstream. If an inert partition layer is disposed between the inner active layer 40 and the core 30, then the inert partition layer is dissolved prior to exposure of the core 30.

Once the core 30 is exposed, the core 30 can be digested in the manner indicated. In one example, the core 30 can be chewed and swallowed. For instance, as described above, the core 30 can be defined by a food product that is intended for gastrointestinal digestion. Accordingly, the core API is similarly subjected to gastrointestinal digestion. In other examples, the core 30 can be configured to dissolve against the mucosa if desired. In some examples, the edible body 54 can be configured to provide the user with indicia that indicates that the active layers have been dissolved and the edible body 54 is ready to be chewed and swallowed. In this regard, the core 30 can have a different flavor profile than at least one or more up to all of the active layers. The active layers can have the same flavor profile or different flavor profiles. The user can be informed of the flavor profile of each of the at least one active layer 22 and the flavor profile of the core 30. Thus, when the user can taste the flavor of the core and none of the flavors of the at least one active layer 22, the user can conclude that the core 30 is ready to be chewed and swallowed. Alternatively or additionally the sensory indicia may be incorporated into the partition layers rather than the active layers.

This arrangement of sequential layers and signaling properties represents a new generation of "functional or configurable edibles". In other words, layered edible products can be configured to deliver the desired effects of the APIs at a predetermined time. Thus, kits of layered edible products can include different inner APIs, different core APIs if present, and different outer layers, if present, in any combinations as desired, as described herein. The end user can select a layered edible product for consumption among a kit of available layered edible products that best corresponds to the desired therapeutic effects of the end user, which may be best optimized by selecting the layered edible product having the desired API chemistries of the inner layer, the core (if present), and the outer layer (if present) along with their respective desired time durations. The layered edible products 20 can be substantially (within manufacturing tolerances) identical to each other in size and shape.

Figure 4A:
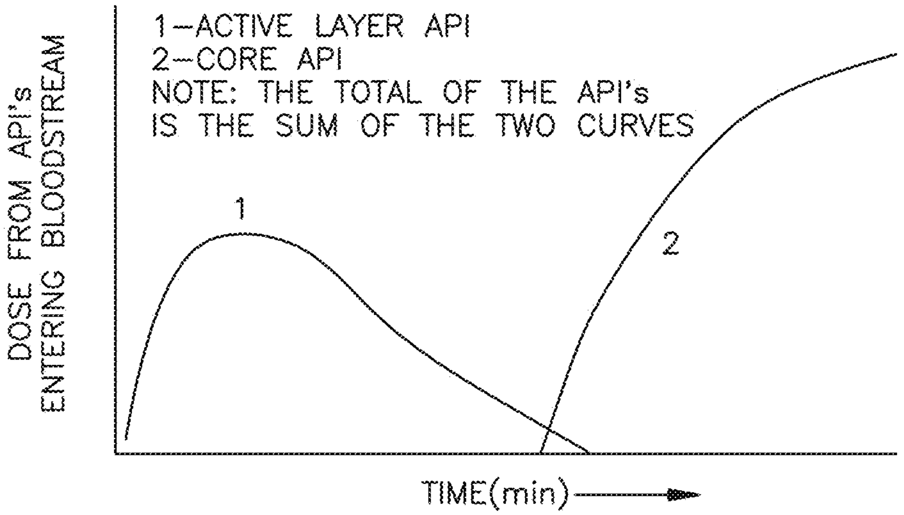
FIG. 4A is a schematic chart illustrating the dose of API entering the bloodstream as a function of time in minutes from a layered edible that includes a core and a single active layer.

Referring now also to FIG. 4A, and as described above with respect to FIGS. 1A-3B, the layered edible product 20 can be configured to release the API of the at least one active layer 22 prior to releasing the API of the core 30. In particular, when the inner active layer 40 is the only active layer of the layered edible product, the inner API is absorbed into the bloodstream through the mucosa, which can deliver a rapid response. In some examples, the therapeutic effect of the inner API begins ramping up in the body within minutes, such as between 5 to 10 minutes. Continued transmucosal absorption of the inner API will, of course, cause the therapeutic effect to continue. The therapeutic effect of the inner API can extend beyond the point in time that the inner active layer 40 has been fully absorbed and until such time that the inner API concentration in the bloodstream has been removed by the metabolism of the consumer. Once the inner active layer 40 has been fully absorbed, then the core 30 can be exposed and consumed. If a transition layer is disposed between the inner active layer 40 and the core 30, then the transition layer is ingested prior to ingesting the core 30.

It is appreciated that once the inner active layer 40 has been completely dissolved, the therapeutic effect delivered by the inner API in the bloodstream continues for a period of time until ramping down. The inner active layer 40 and the core 30 can be configured such that the core API begins ramping up its therapeutic effect while the therapeutic effect of the inner API is ramping down. This is achieved if the user selects, as the effect of the inner API is diminishing, to begin chewing the entire remaining edible (which is mainly the core) and allowing the chewed core material to linger in the mouth, before swallowing, so as to be partially absorbed through the sublingual mucosa. This initial sublingual absorption of the core API can provide an early initiation of the overall core API effect prior to gastrointestinal digestion. Without the initial sublingual absorption of the core API, the substantial entire therapeutic effect of the core API will be achieved solely by the usual gastrointestinal digestive route. Alternatively, the inner active layer 40 and the core 30 can be configured such that the core API begins ramping up its therapeutic after the therapeutic effect of the inner API has substantially ceased. Either way, it should be appreciated that the layered edible product 20 is configured to cause the body to experience the therapeutic effect of the inner API, followed by the therapeutic effect of the core API. Further, the gastrointestinally digested core API can deliver its therapeutic effect for a longer time duration than the mucosal ingested inner API. In one example, the therapeutic effect of the core API can last multiples of the time duration of the therapeutic effect of the inner API.

Figure 4B:
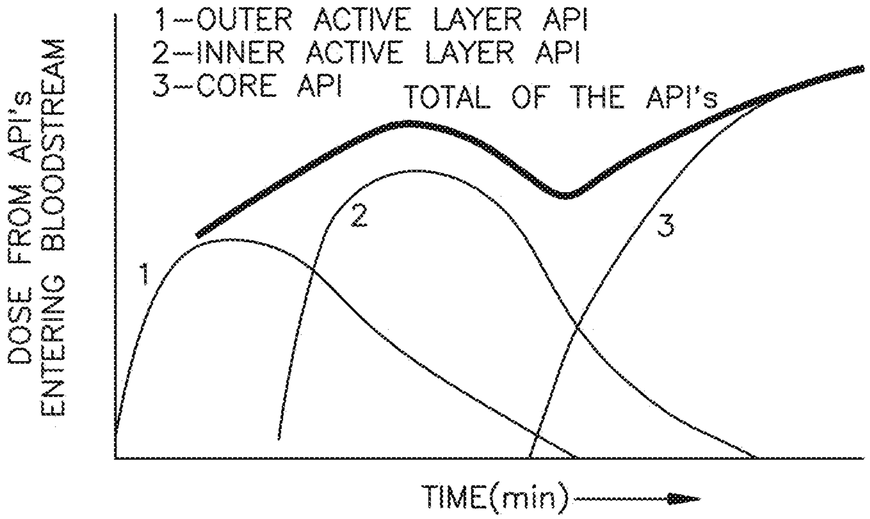
FIG. 4B is a schematic chart illustrating the dose of API entering the bloodstream as a function of time in minutes from a layered edible that includes a core and both an inner and outer active layers.

Referring now to FIG. 4B, when the layered edible product 20 includes the inner active layer 40 and the outer active layer 42, the outer API is absorbed into the bloodstream through the mucosa, which can deliver a rapid response as described in the previous paragraphs. In some examples (see curve 1 in FIG. 4B), the therapeutic effect of the outer API begins ramping up in the body within minutes, such as between 5 to 10 minutes. Continued transmucosal absorption of the outer API will, of course, cause the therapeutic effect to continue. Once the outer active layer 42 has been substantially absorbed (as at the peak of curve 1 in FIG. 4B), then the partition layer 52 disposed between the outer active layer 42 and the inner active layer 40 can begin dissolving and the inner active layer 40 can be exposed and absorbed (curve 2 in FIG. 4B). Thus, the layered edible product 20 can be designed such that the inner active layer 40 is absorbed while the therapeutic effect of the outer layer 42 API is still extant in the bloodstream, as depicted in FIG. 4B by the overlapping curves 1 and 2.

Alternatively, the layered edible product 20 can be configured such that the inner API begins ramping up its therapeutic after the therapeutic effect of the outer API has substantially ceased. Alternatively still, if it is desired to stack the effects of the inner and outer APIs, the layered edible product 20 can be configured such that the inner API begins ramping up its therapeutic effect before the therapeutic effect of the outer API has concluded. Either way, it should be appreciated that the layered edible product 20 is configured to cause the body to first experience the therapeutic effect of the outer API, followed by the therapeutic effect of the inner API. It should be appreciated, of course, that the therapeutic effects of the inner and outer APIs can last for different time durations as desired. Once the inner active layer 40 has been absorbed, the core 30 can then be consumed in the manners described above.

Figure 4C:
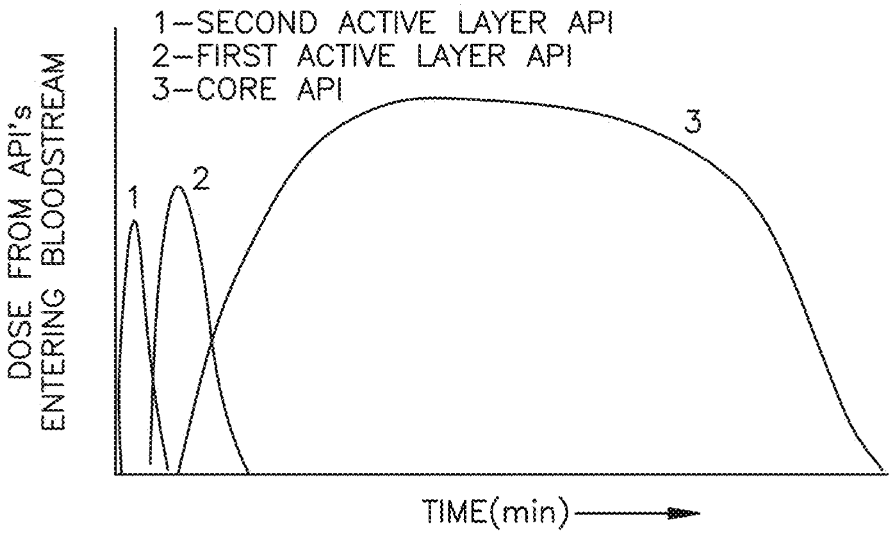
FIG. 4C is a schematic chart similar to FIG. 4B but over a ten-times longer span of time (in hours) that includes brief API deliveries from the two layers and much longer-duration delivery from the core.

It should be appreciated that either or both of the duration of the therapeutic effect of any of the APIs described herein and the dosage that enters the bloodstream of any of the APIs described herein can be adjusted as desired. As illustrated in FIGS. 4B-4C, the dosage of the inner API that enters the bloodstream can be greater than the dosage of the outer API that enters the bloodstream. Alternatively, the dosage of the inner API that enters the bloodstream can be less than or substantially equal to the dosage of the outer API that enters the bloodstream. Similarly, the API of each active layer can have a greater dosage, less dosage, or substantially equal dosage compared to the core API. As illustrated FIG. 4C, the duration of the therapeutic effect of the core API can be greater than each of the outer API and the inner API, both alone and in combination, due to the far greater physical extent of the digestive path in the body.

It is recognized that when the active layer(s) and optionally the core are sequentially placed against the select mucosa to undergo transmucosal absorption, a portion of the respective API is likely to be swallowed with saliva. However, it is also appreciated that some of the respective API, which can be a majority of the respective API, up to substantially all of the respective API, will undergo transmucosal absorption, thereby providing a more immediate therapeutic effect than if the entire layered edible product were to be chewed and swallowed. Furthermore, the form of the API employed in the active layer(s) and optionally the core can employ any of the various *cannabis* forms (liposomes, emulsions, solid-lipid nanoparticles, self-nano-emulsifying drug delivery system (SNEDDS) particles, and the like).

Referring now to FIGS. 6A-6D generally, one method and apparatus for delivering at least one API in the form of microdroplets to each of the core and active layers will be described. It should be appreciated that this is only one example showing delivery of the at least one API, and all other methods for dosing the core 30 with an API and fabricating each active layer are also contemplated herein. As illustrated in FIGS. 6A-6D, a dosing system 62 can include at least one reservoir 73 that contains a respective API, and at least one dosing station 64 that receives at least one API from the at least one reservoir 73 and delivers the API to an underlying substrate, and at least one conveyor 70 that brings the substrate into alignment with a dosing head 68 of the dosing station 64. One or more dosing stations 64 can be used to dose the core 30 with the core API, to dose or fabricate the inner active layer 40 with the inner API, and/or to dose the outer active layer 42 with the outer API. For instance, a single dosing station 64 can selectively deliver multiple APIs from respective ones of the reservoirs 73. The reservoirs 73 can include the core API, the inner API, and the outer API respectively. Alternatively, multiple dosing stations 64 can each be placed in communication with a respective dedicated one of the reservoirs 73, such that different dosing stations 64 deliver the core API, the inner API, and the outer API. The dosing station 64 can be configured as described in U.S. patent application Ser. No. 16/865,094 filed May 1, 2020, the disclosure of which is hereby incorporated by reference as if set forth in its entirety herein.

Figure 6A:
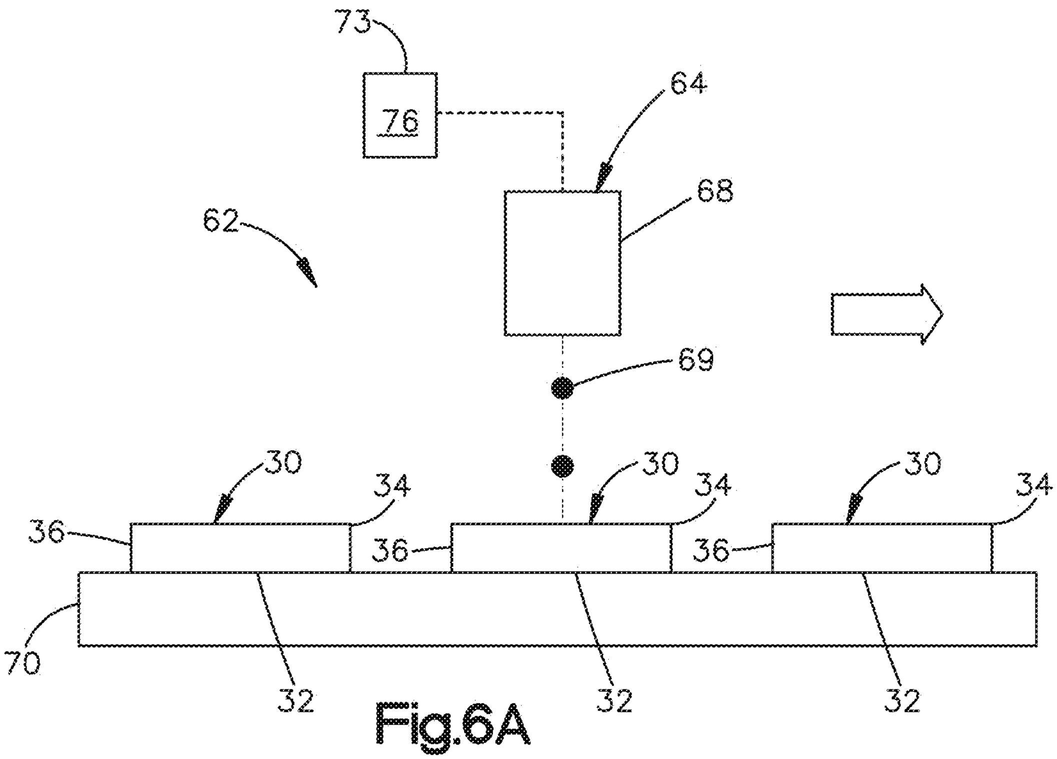
FIG. 6A is a schematic side elevation view of a dosing station shown delivering a core API to the core.

Referring now to FIG. 6A, the dosing station 64 is shown delivering the core API 66 from the at least one dosing head 68 to the core 30. In particular, the core 30 can be brought into alignment with the dosing head 68 by moving the core 30 into alignment with the dosing head 68 and/or moving the dosing head 68 into alignment with the core 30. In one example, the core 30 can be disposed on the conveyor 70 that delivers the core 30 to a position in alignment with the at least one dosing head 68. The core API 66 can then be delivered from the dosing head 68 to the core 30 under gravitational forces so as to define the core API. In one example, the core API 66 can include any number of constituent components of the *cannabis* group described above. Alternatively or additionally, the core API 66 can include any suitable prescription drug or over-the-counter drug or nutraceutical as desired. In some examples, once the core API 66 has been delivered to one surface of the core 30, the core can be flipped so that the core API 66 is subsequently delivered to an opposite surface of the core 30. The one surface and the opposite surface can be defined by the core inner surface 32 and the core outer surface 34, respectively. In some examples, at least a portion up to a substantial entirety of the core API 66 can be disposed on the core external surface 33. Alternatively or additionally, at least a portion up to a substantial entirety of the core API 66 can be absorbed by the core 30.

In one example, the core API 66 can be delivered to the core 30 as successive microdroplets 69 in the manner described in Appendix A. The microdroplets 69 can be delivered from the dosing head 68 under gravitational forces along a dosing API axis 79. Alternatively, the core API 66 can be delivered as a stream, as a spray, as conventional droplets, as an emulsion, or in any suitable alternative form as desired. For instance, the API can be delivered to the substrate as a powder. Alternatively, the API can be delivered as an injection into the core 30.

As noted above, the core API 66 can be delivered to the substrate 30 in accordance with any suitable alternative method. As described above, in some examples the substrate 30 can be a cooked food product. In particular, a mixture of ingredients optionally including an API can be cooked and singulated (or singulated then cooked) to define a corresponding plurality of substrates. In one example, the core API 66 can be added as part of the substrate fabrication process. For instance, the core API 66 can be delivered to the ingredients or the mixture prior to cooking the mixture as desired so as to define the substrate 30 having the at least one substrate API. Alternatively still, the core 30 having the core API 66 can be procured from any suitable manufacturer or retailer.

Figure 6B:
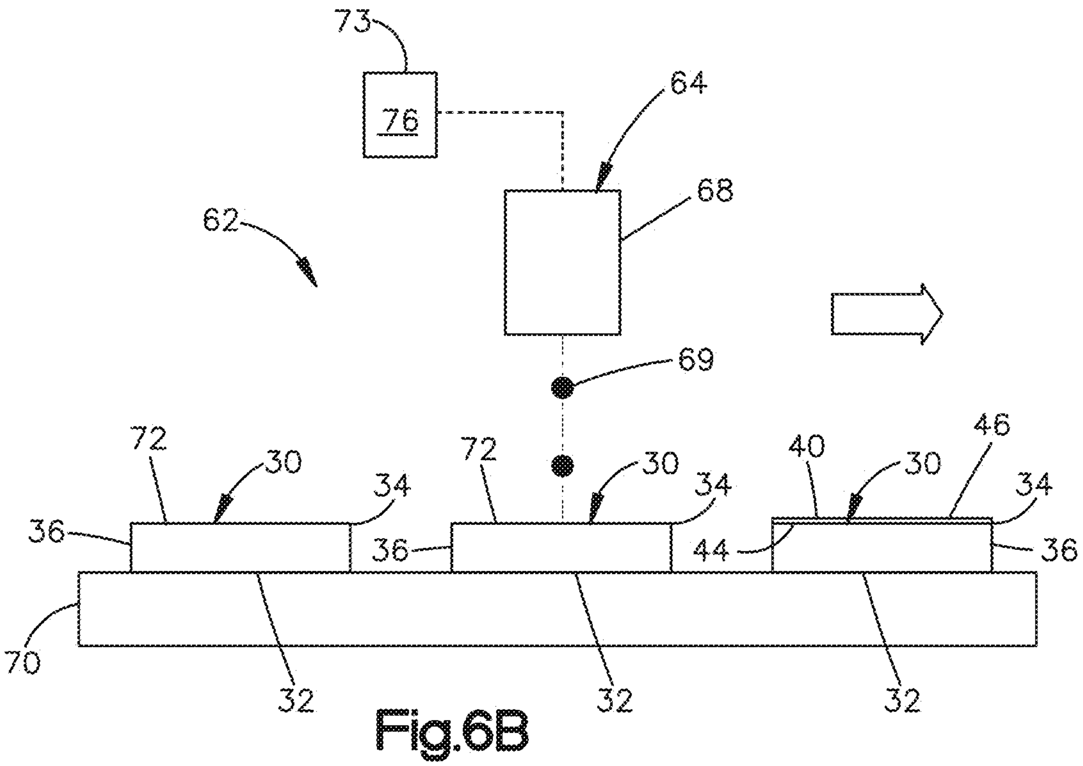
FIG. 6B is a schematic side elevation view of a dosing station shown delivering an inner API to the core of FIG. 6A so as to define an inner active layer disposed over the core.

Referring now to FIG. 6B, the inner API 67 of the inner active layer 40 can be applied to a first underlying outer surface 72. Thus, the inner active layer 40 can be disposed directly on the first underlying outer surface 72. In one example, the first underlying outer surface 72 can be defined by the core 30. In examples whereby the core API 66 is delivered to the core 30, the inner active layer 40 can be delivered to the core 30 after the core API 66 has been delivered to the core 30, or after the API-containing core 30 has been procured. Alternatively, the inner active layer 40 can be delivered to the core 30 that is inert, and thus does not contain an API. In other examples, a partition layer of the type described above can be applied over, such as onto, the substrate 30, and the first underlying surface 72 can thus be defined by the partition layer. The inner active layer 40 can therefore be applied to the first underlying surface 72 as defined by the partition layer.

In particular, the core 30 can be brought into alignment with the dosing head 68 by moving the core 30 into alignment with the dosing head 68 and/or moving the dosing head 68 into alignment with the core 30. In one example, the core 30 can be disposed on a conveyor 70 that delivers the core 30 to a position in alignment with the at least one dosing head 68. The inner API 67 can then be delivered from the dosing head 68 to the core 30 (or partition layer disposed over the core 30) under gravitational forces so as to define the inner active layer 40. In some examples, once the inner API 67 has been delivered to the core 30 or partition layer, the core can be flipped so that the inner API 67 is subsequently delivered to an opposite surface of the core 30 or partition. The one surface and the opposite surface can be defined by the core inner surface 32 to the core outer surface 34, respectively. Alternatively, the one surface and the opposite surface can be defined by the partition. Alternatively still, one of the surfaces can be defined by the core and the other of the surfaces can be defined by the partition.

In one example, the inner API 67 can include any number of constituent components of the *cannabis* group described above. Alternatively or additionally, the inner API 67 can include any suitable prescription drug or over-the-counter drug or nutraceutical as desired. As described above, at least one of the constituent components of the inner API 67 can be different than the core API 66. Alternatively or additionally, at least one of the constituent components of the core API 66 can be different than the inner API 67. It should be further appreciated that at least one common constituent components can be included in both the core API 66 and in the inner API 67. However, at least one common constituent component of the common constituent components can be included in a different quantity in the inner API 67 with respect to the core API 66. For instance, as described above, the at least one common constituent component can be THC, CBD, and/or any suitable alternative constituent component as desired.

In one example, the inner API 67 can be delivered as successive microdroplets 69 in the manner described in Appendix A. The microdroplets 69 can be delivered from the dosing head 68 under gravitational forces. Alternatively, the inner API 67 can be delivered as a stream, as a spray, as conventional droplets, as an emulsion, or in any suitable alternative form as desired. The inner API 67 can define a layer that extends over the first underlying surface 72. It should be appreciated, of course, that the inner active layer 40 can be alternatively constructed as desired. For instance, the core 30 can be submersed in or otherwise exposed to a bath of the inner API 76 to produce the inner active layer 40 on the core 30 or partition layer disposed on the core 30. For instance, the API can be delivered as a powder.

Figure 5A:
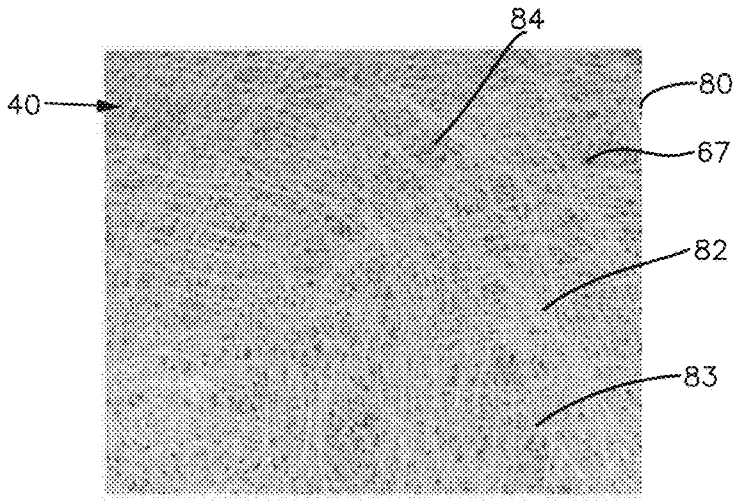
FIG. 5A is a perspective view of an inner carrier configured to receive an API so as to define an active layer in one example.

Referring now also to FIG. 5A, while the inner API 67 can be applied directly to the first underlying surface 72 in the manner described above, it should be appreciated that in other examples that the inner active layer 40 can include an inner carrier member 80 that is applied to or otherwise supported by the first underlying surface 72. The inner carrier member 80 can carry the inner API 67. In one example, the inner API 67 can be delivered to the inner carrier member 80. The inner carrier member 80 can be configured as a mat, slip, strip, or other suitable structure that is configured to be supported by the underlying surface 72. In some examples, the inner carrier member 80 can be discrete and adhered or otherwise joined to the first underlying surface 72. In other examples, the inner carrier member 80 can be 3D printed onto the first underlying surface 72. The inner carrier member 80 can define an inner material matrix 82 that can be configured to absorb the inner API 67. Alternatively or additionally, the inner API 67 can coat the inner material matrix 82. Alternatively or additionally still, the inner material matrix 82 can define a plurality of pores 84 that are sized and configured to receive the inner API 67. For instance, the inner material matrix 82 can be defined by a plurality of filaments 83 that can define the pores 84. In one example, the filaments 83 can be defined by one or more layers of a polymeric protein that are networked so as to define the pores 84. The inner material matrix 82 can be defined by any suitable material that can dissolve against a mucosal surface when the inner API 67 is configured to be transmucosally delivered to the bloodstream. The mucosal surface can be defined by the sublingual mucosa 24 or the buccal mucosa 26 (see FIGS. 1A-1B). For instance, the material matrix 82 can include any one or more of sugar, salt, dissolvable strips that include water-soluble polymers, or the like. In some examples, the material matrix 82 can be dissolvable strips that dissolve in the oral cavity. The inner API 67 can be delivered or otherwise applied to the inner carrier member 80 in any manner described herein so as to define the inner active layer 40.

Figure 6C:
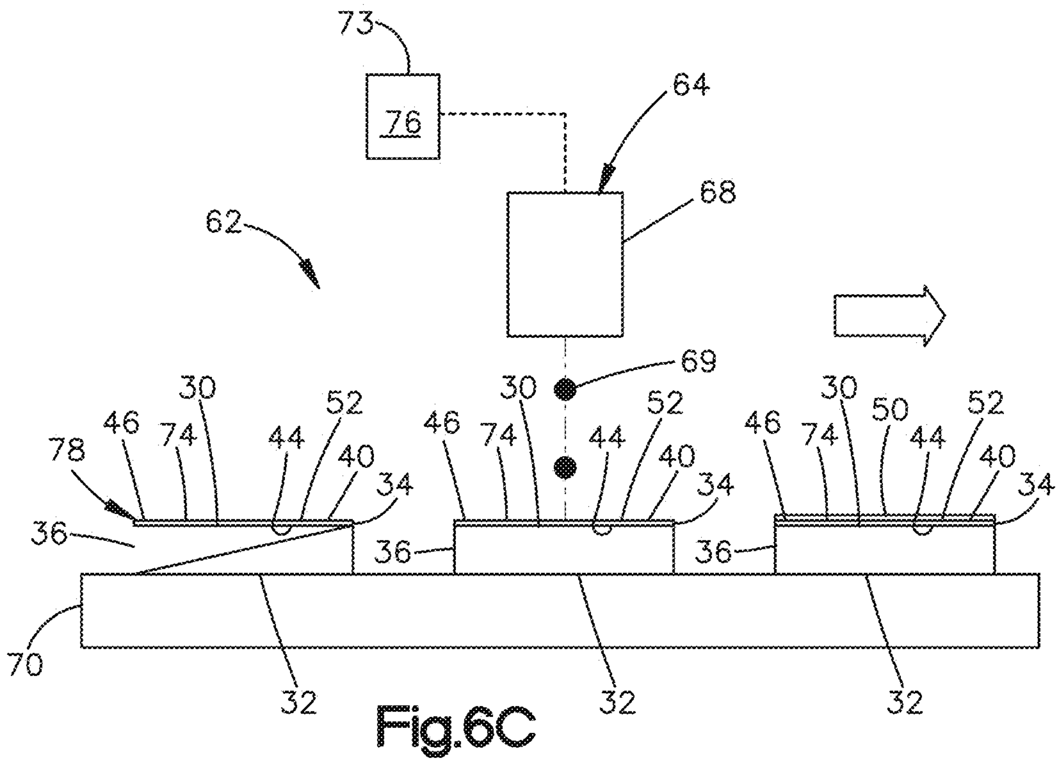
FIG. 6C is a schematic side elevation view of a dosing station shown delivering an outer API to a partition that is disposed over the inner active layer so as to define an outer active layer disposed on the partition and thus disposed over the inner active layer.

Referring now to FIG. 6C, the partition layer 52 can be disposed on the inner active layer 40. The partition layer 52 be applied in any suitable manner known by those having ordinary skill in the art of food science, including but not limited to powder deposition, baths, droplets, sprays, and the like. Thus, the partition layer 52, and in particular the outer partition surface 56, can define a second underlying outer surface 74. The outer active layer 42 can be delivered to the second underlying outer surface 74 as defined by the outer partition layer 52, in one example. Alternatively, as will be described in more detail below, the second underlying outer surface 74 can be defined by the inner active layer 40. In one example, a composite structure 78 including the core 30, the inner active layer 40, and the partition 52 (if present) disposed on the inner active layer 40 (with or without a partition layer between the core 30 and the inner active layer 40) can be brought into alignment with the dosing head 68 by moving the composite structure 78 into alignment with the dosing head 68 and/or moving the dosing head 68 into alignment with the composite structure 78. In one example, the composite structure 78 can be disposed on the conveyor 70 that delivers the composite structure 78 to a position in alignment with the at least one dosing head 68. The outer API 76 can then be delivered from the dosing head 68 to the composite structure 78, and in particular to the second underlying outer surface 74 under gravitational forces so as to define the outer active layer 42. In some examples, once the outer API 76 has been delivered to the second underlying outer surface 74, the composite structure 78 can be flipped so that the outer API 76 is subsequently delivered to an opposite surface of the composite structure 78. The opposite surface can be defined by the partition layer 52 in one example. Alternatively, the opposite surface can be defined by the inner active layer 40. Alternatively still, the opposite surface can be defined by the core 30.

In one example, the outer API 76 can include any number of constituent components of the *cannabis* group described above. Alternatively or additionally, the outer API 76 can include any suitable prescription drug or over-the-counter drug or nutraceutical as desired. As described above, at least one of the constituent components of the outer API 76 can be different than either or both of the core API 66 and the inner API 67. Alternatively or additionally, at least one of the constituent components of either or both of the core API 66 and the inner API 67 can be different than the outer API 76. It should be further appreciated that at least one common constituent components can be included in either or both of the inner API 67 and the core API 66, and in the outer API 76. However, at least one common constituent component of the common constituent components can be included in a different quantity in the outer API 76 with respect to either or both of the inner API 67 and the core API 66. For instance, as described above, the at least one common constituent component can be THC, CBD, and/or any suitable alternative constituent component as desired.

In one example, the outer API 76 can be delivered as successive microdroplets 69 in the manner described in Appendix A. The microdroplets 69 can be delivered from the dosing head 68 under gravitational forces. Alternatively, the outer API 76 can be delivered as a stream, as a spray, as conventional droplets, as an emulsion, or in any suitable alternative form as desired. The outer API 76 can define a layer that extends over the first underlying surface 72. Alternatively, the composite structure 78 can be submersed in or otherwise exposed to a bath of the outer API 76 to produce the outer active layer 42 on the partition layer 52. It should be appreciated, of course, that the outer active layer 42 can be alternatively constructed as desired. For instance, the outer API 76 can be delivered as a powder. In other examples, the outer API 76 can be delivered to a discrete layer or can form a discrete layer that is subsequently adhered or otherwise joined to the first underlying surface 72.

Figure 6D:
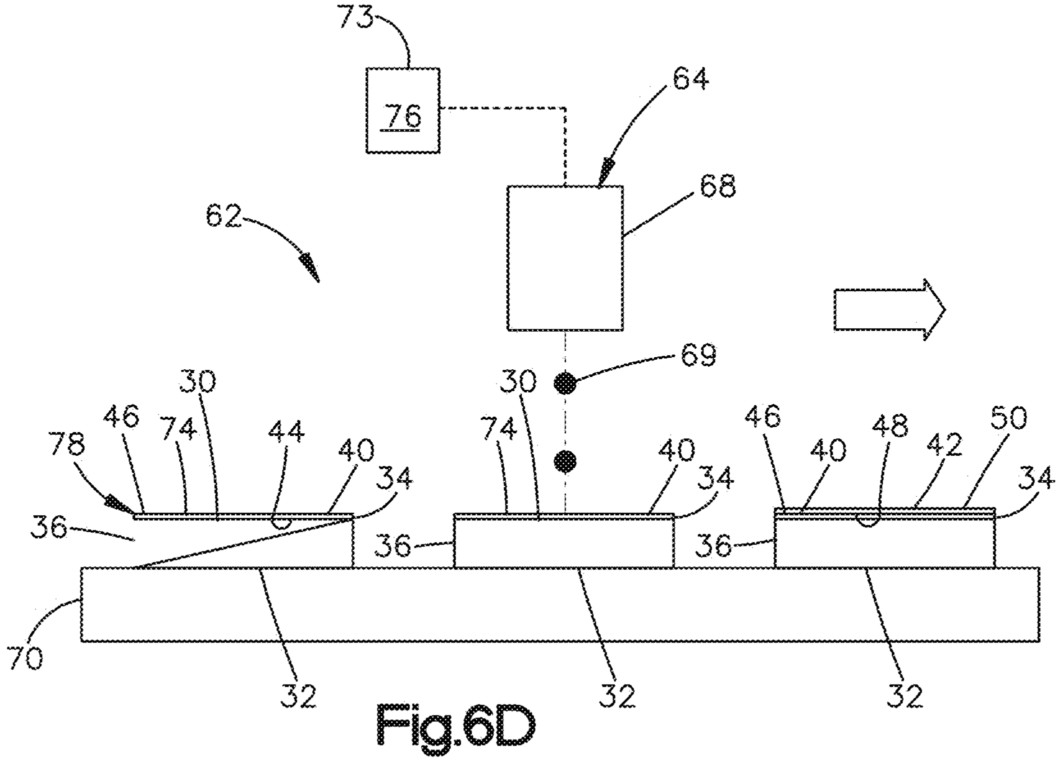
FIG. 6D is a schematic side elevation view of a dosing station shown delivering an outer API to directly to the inner active layer so as to define an outer active layer disposed on the inner active layer.

Referring now to FIG. 6D, and as described above, the composite structure 78, and thus the resulting edible body 54, can be devoid of the partition layer 52 between the inner active layer 40 and the outer active layer 42. Thus, the inner active layer 40, and in particular the outer surface 46, can define the second underlying outer surface 74. The outer API 76 can be delivered directly to the second underlying outer surface 74 as defined by the inner active layer 40 so as to define the outer active layer 42. In one example, the composite structure 78 including the core 30 and the inner active layer 40 without the partition layer disposed between the inner and outer active layers 40 and 42, respectively, (with or without a partition layer between the core 30 and the inner active layer 40) can be brought into alignment with the dosing head 68 by moving the composite structure 78 into alignment with the dosing head 68 and/or moving the dosing head 68 into alignment with the composite structure 78. In one example, the composite structure 78 can be disposed on the conveyor 70 that delivers the composite structure 78 to a position in alignment with the at least one dosing head 68. The outer API 76 can then be delivered from the dosing head 68 to the composite structure 78, and in particular to the inner active layer 40, under gravitational forces so as to define the outer active layer 42. In some examples, once the outer API 76 has been delivered to the inner active layer 40, the composite structure 78 can be flipped so that the outer API 76 is subsequently delivered to an opposite surface of the composite structure 78. The one surface and the opposite surface can be defined by the inner active layer 40 in one example.

In one example, the outer API 76 can be delivered as successive microdroplets 69 in the manner described in Appendix A. The microdroplets 69 can be delivered from the dosing head 68 under gravitational forces. Alternatively, the outer API 76 can be delivered as a stream, as a spray, as conventional droplets, as an emulsion, or in any suitable alternative form as desired. Alternatively, the composite structure 78 can be submersed in or otherwise exposed to a bath of the outer API 76 to produce the outer active layer 42 on the inner active layer 40. It should be appreciated, of course, that the outer active layer 42 can be alternatively constructed as desired. For instance, the outer API 76 can be delivered as a powder. In other examples, the outer API 76 can be delivered to a discrete layer or can form a discrete layer that is subsequently adhered or otherwise joined to the first underlying surface 72.

Figure 5B:
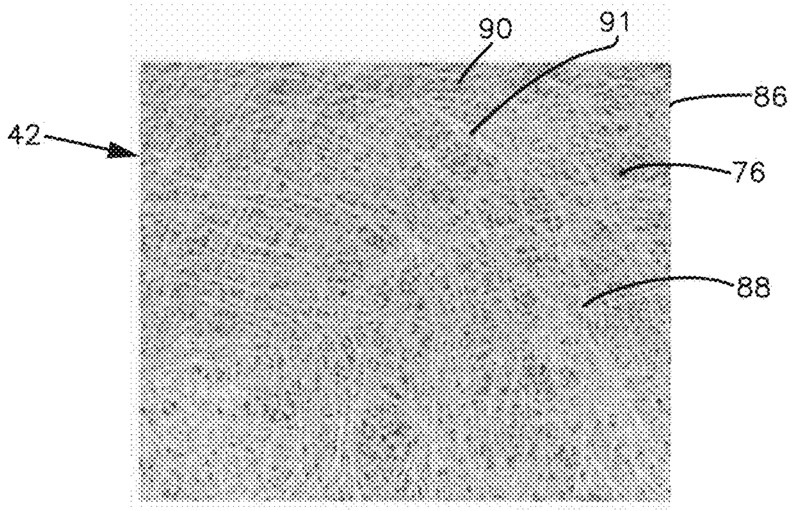
FIG. 5B is a perspective view of an outer carrier member configured to receive an API so as to define an active layer in one example.

Referring now to FIG. 5B, while the outer API 76 can be applied directly to the second underlying surface 74 in the manner described above, it should be appreciated that in other examples that the outer active layer 42 can include an outer carrier member 86 that is applied to or otherwise supported by the second underlying surface 74. The outer carrier member 86 can, in turn, carry the outer API 76. In one example, the outer API 76 can be delivered to the outer carrier member 86. The outer carrier member 86 can be configured as a mat, slip, strip, or other suitable structure that is configured to be supported by the second underlying surface 74. In some examples, the outer carrier member 86 can be discrete and adhered or otherwise joined to the second underlying surface 74. In other examples, the outer carrier member 86 can be 3D printed onto the second underlying surface 74. The outer carrier member 86 can define an outer material matrix 88 that can be configured to absorb the inner API 67. Alternatively or additionally, the inner API 67 can coat the outer material matrix 88. Alternatively or additionally still, the outer material matrix 88 can define a plurality of pores 90 that are sized and configured to receive the outer API 76. For instance, the outer material matrix 818 can be defined by a plurality of filaments 91 that can define the pores 90. In one example, the filaments 91 can be defined by one or more layers of a polymeric protein that are networked so as to define the pores 90. The outer material matrix 88 can be defined by any suitable material that can dissolve against a mucosal surface when the outer API 76 is configured to be transmucosally delivered to the bloodstream. For instance, the outer material matrix 88 can include any one or more of sugar, salt, water-soluble polymers, or the like. In some examples, the outer material matrix 88 can be dissolvable strips that dissolve in the oral cavity. The outer API 76 can be delivered or otherwise applied to the outer carrier member 86 in any manner described herein so as to define the outer active layer 42.

Figure 5C:
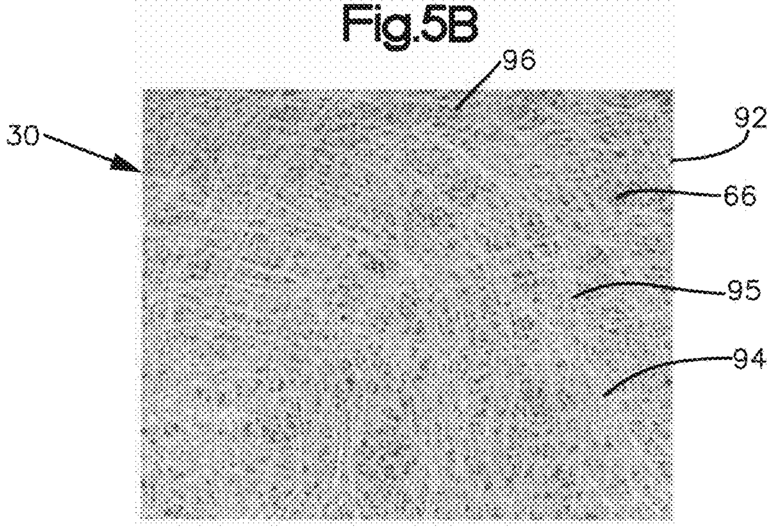
FIG. 5C is a perspective view of an outer carrier member configured to receive an API so as to define a core in one example.

Referring now to FIG. 5C, in some examples the core 30 can be dissolvable against a mucosal surface in the oral cavity. The core 30 can therefore be constructed in accordance with any example described herein with respect to the inner and outer active layers 40 and 42. For instance, the core can include a core carrier member 92 that can carry the core API 66 if present. The core carrier member 92 can be configured as a mat, slip, strip, or other suitable structure that can define the underlying surface 72 for the inner core layer 40 (see FIG. 6B). The core carrier member 92 can define a core material matrix 94 that can be configured to absorb the core API 66. Alternatively or additionally, the core API 66 can coat the core material matrix 94. Alternatively or additionally still, the core material matrix 94 can define a plurality of pores 96 that are sized and configured to receive the core API 66. For instance, the core material matrix 94 can be defined by a plurality of filaments 95 that can define the pores 96. In one example, the filaments 95 can be defined by one or more layers of a polymeric protein that are networked so as to define the pores 96. The core material matrix 94 can be defined by any suitable material that can dissolve against a mucosal surface when the core API 66 is configured to be transmucosally delivered to the bloodstream. The mucosal surface can be defined by the sublingual mucosa 24 or the buccal mucosa 26 (see FIGS. 1A-1B). For instance, the core material matrix 94 can include any one or more of sugar, salt, dissolvable strips that include water-soluble polymers, or the like. When the core material matrix 94 is dissolvable against the mucosal surface, the core API 66 can enter the undergo transmucosal absorption into the bloodstream.

In other examples, the core carrier member 92 can be gastrointestinally digestible. For instance, the core 30 can be placed against the mucosal surface such that at least a portion up to an entirety of the core API 66 can undergo transmucosal absorption into the bloodstream. The core 30 can then be masticated and swallowed. Alternatively, when the carrier member of the core 30 is gastrointestinally digestible, the core 30 be masticated and swallowed such that the core API undergoes gastrointestinal digestion in the manner described above. In still other examples, the core carrier member 92 can be configured not to dissolve against the mucosal surface, and can be further configured not to be swallowed. In such examples, the core carrier member 92 can be placed against the mucosal surface so that the core API can undergo transmucosal absorption into the bloodstream in the oral cavity. Once the core API has been absorbed, the core carrier member 92 can be ejected from the oral cavity.

Any number of additional intermediate active layers can be added to the composite structure as desired between the inner active layer 40 and the outer active layer 42 as desired. The intermediate active layers can be constructed in accordance with any of the active layers described herein. The intermediate active layers can be separated from each other by a respective partition layer as described herein, or can contact each other directly. An innermost one of the intermediate active layers can be disposed adjacent the inner active layer 40 with or without a partition layer disposed therebetween, and an outermost one of the intermediate active layers can be disposed adjacent the outer active layer 42 with or without a partition layer disposed therebetween.

As described above with respect to FIGS. 1-6D, any API-containing portion(s) of the layered edible product 20, such as the core 30, the at least one active layer 22 including the inner active layer 40 and the outer active layer 42 if present, can be configured as continuous bodies in one example. Alternatively, referring now to FIGS. 7A-7D, an API 98 is shown patterned on an underlying surface 103 of a carrier member 100. It should be appreciated that any one or more up to all of the core API 66, the inner API 67, the outer API 76 can be configured as shown by the API 98. Similarly, the underlying surface defined by any one or more up to all of the inner carrier member 80, the outer carrier member 86, and the core carrier member 92 can be configured as the underlying surface 103 of the carrier member 100. Alternatively, either or both of the first and second underlying surfaces 72 and 74 can be defined by the carrier member 100.

Figure 7A:
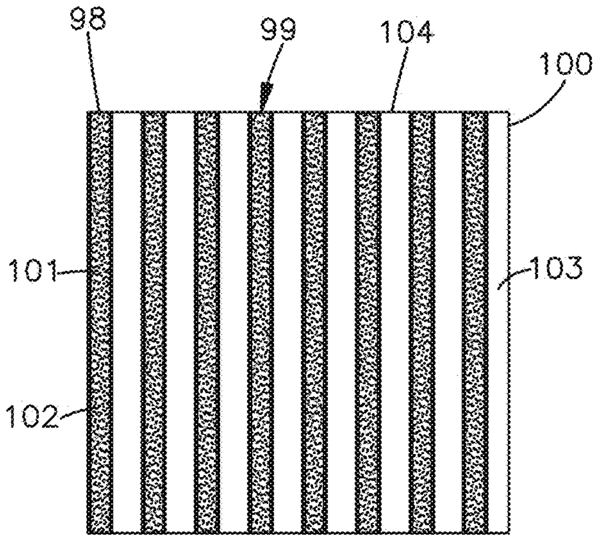
FIG. 7A is a schematic top plan view showing a pattern of lines of deposited API in one example.
Figure 7B:
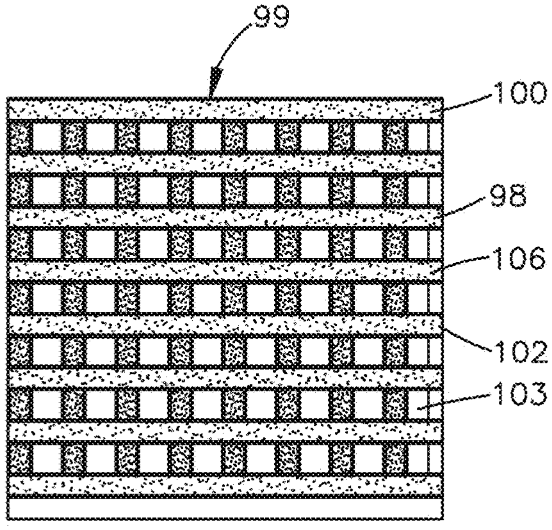
FIG. 7B is a schematic top plan view showing a pattern of square pixels of API in another example.

As shown at FIG. 7A, the API 98 can be arranged on an underlying surface 103 that is defined by a carrier member 100 into any predetermined pattern as desired. The predetermined pattern can be applied to an outermost active surface of the layered edible product 20 described above, which can be defined by a wrapper or an outer active layer (which can be the sole active layer or an outermost one of a plurality of active layers). The predetermined pattern can define any suitable shape or design. For instance, the pattern 99 of the API 98 can include a plurality of alternating structures 101, such as alternating lines 102 separated by gaps 104. Thus, the pattern 99 of the API 98 can define a plurality of lines 102 and a plurality of gaps 104 that extend between the lines 102 and are alternatingly arranged with the lines 102. The gaps 104 can be devoid of the API 98 or include less of the API 98 than the lines 102. The lines 102 can be straight, curved, or otherwise shaped as desired. In other examples, such as shown in FIG. 7B, the lines 102 can define a grid 106, whereby perpendicular lines 102 are arranged as respective rows and columns defined by the API 98 intersect. The lines 102 can define at right angles or any alternative angle as desired. The lines 102 can be individual separate lines or can be adjoined to each other, for instance at their ends. In some examples, the pattern 99 can be defined such that the API 98 is positioned to match an average distance between a particular class of taste buds on the mucosal surface. In another example, the pattern 99 of the API 98 can define any suitable shape, such as a concentric circular ring pattern a horseshoe pattern so as to substantially match the geometry of the taste sensors and absorption zones in the sublingual mucosa or the buccal mucosa.

Figure 7C:
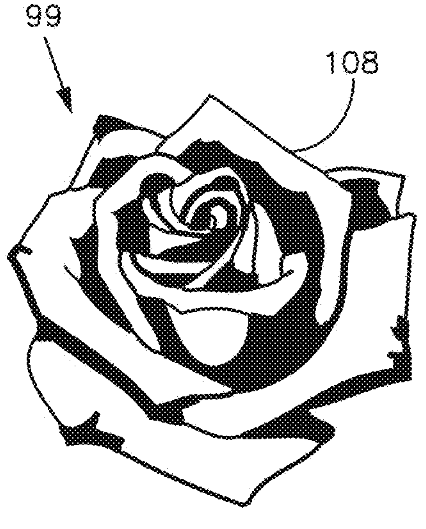
FIG. 7C is a schematic top plan view showing a pattern of API in yet another example.
Figure 7D:
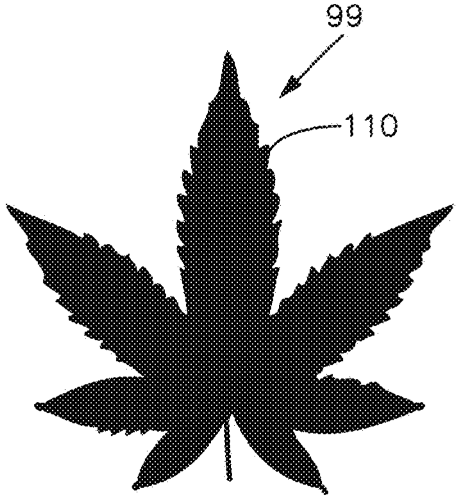
FIG. 7D is a schematic top plan view showing a pattern of API in still another example.

Referring now to FIGS. 7C-7D, the API the pattern 99 described above with respect to FIGS. 7A-7B, and any suitable alternative pattern 99, can be lithographically fabricated, such that a small element of deposition size is defined by of the patterning may be extended in the manner of lithographic patterning. For instance, a node of API deposition is defined by the finest detail along the underlying surface. The node can have a size that is the smallest size of API capable of being deposited by the dosing station in use, or any suitable size as desired. Any image as desired by building a collage of the nodes such that their overall appearance provides the desired pattern 99, which can define the lines and grids of FIGS. 7A-7B, the image of a rose flower 108 shown in FIG. 7C, the image of the *cannabis* leaf governmental symbol 110 shown in FIG. 7D, or any suitable alternative image as desired. In this manner, the API can be 3D printed onto any substrate as desired. Depending on the size of the nodes and limitations of the deposition equipment, the image produced can approach the fine detail of a high-definition black-and-white photograph. The desired pattern 99 can be a graphic indication, such as the symbol 110, that signifies that the layered edible product 20 contains *cannabis* and can further include a numeric or graphical indication of the dosage of the *cannabis*. It should be appreciated that the pattern 99 can alternatively be a graphic indication of any other API of the layered edible product 20, along with the indication of the dosage of the API.

Figure 8A:
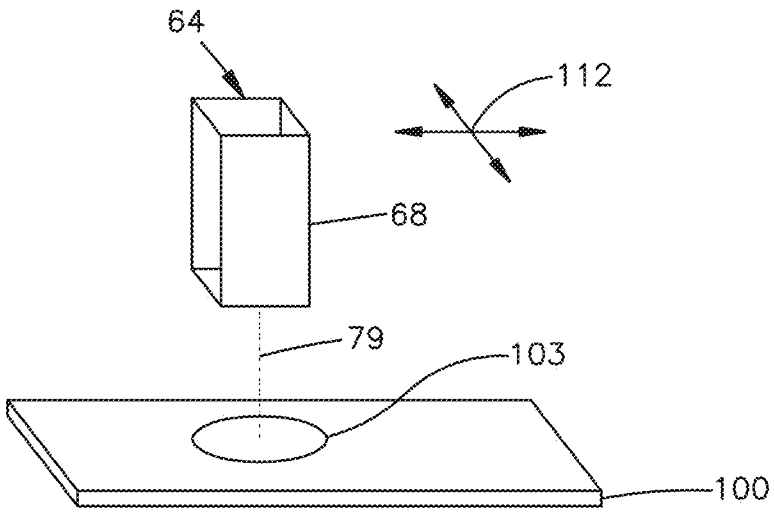
FIG. 8A is a schematic side elevation view of a dosing system wherein the dosing head moves in x or y to create a desired pattern of API on the edible.
Figure 8B:
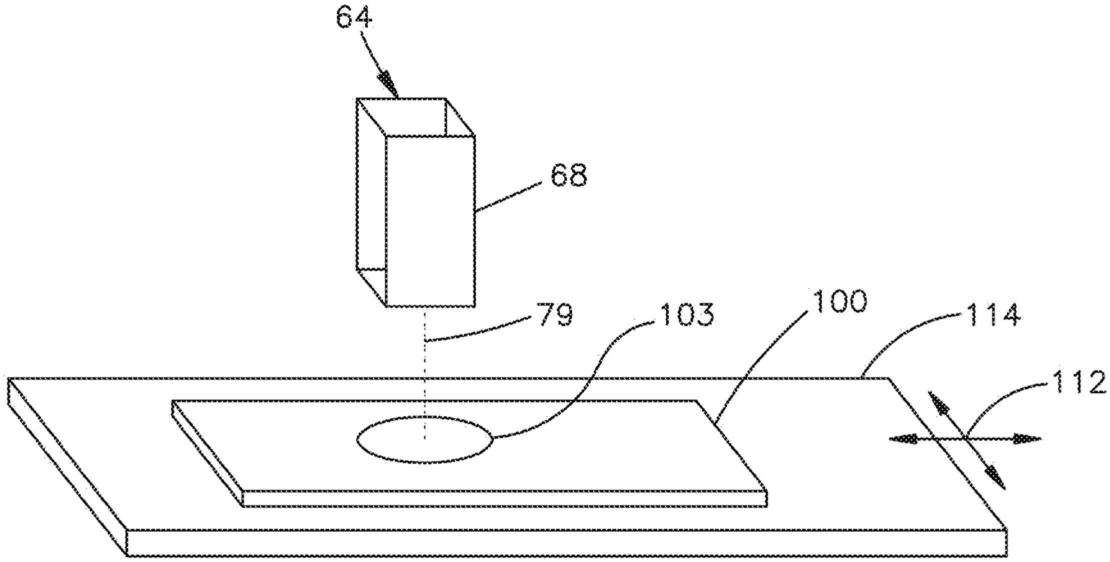
FIG. 8B is a schematic side elevation view of a dosing system wherein the dosing head is fixed in position, but the edible is moved in x or y by a translation system to create a desired pattern of API on the edible.

It is also contemplated that the patterning of API can be achieved with two different approaches. Referring to FIG. 8A, a first approach would employ an imaging capability in the API-deposition assembly such that a section of the desired image (involving multiple elements) could be deposited at once onto a stationary underlying surface 103. The dosing head 68 would then move relative to the underlying surface 103 along a plane 112 that is perpendicular to the dosing axis 79 so as to deliver the API at the desired locations on the underlying surface 103. Referring to FIG. 8B, under a second approach, a transport system is configured to move each edible to nominally locate the underlying surface 103 into alignment with the dosing head 68 that delivers the API along the dosing axis 79. The underlying surface 103 can be disposed on a movable platen 114 that can be moved along the plane 112 under computer control during the deposition of API from the dosing head along the dosing axis until the desired pattern has been deposited. This approach can have the advantage that all of the patterning action is accomplished by the movable stage and computer control without requiring movement of the dosing head. In still other examples, both the dosing head and the underlying stage can be movable to create the desired pattern during delivering of the API from the dosing head.

In should be noted that the illustrations and discussions of the embodiments and examples shown in the figures are for exemplary purposes only and should not be construed as limiting the disclosure. One skilled in the art will appreciate that the present disclosure contemplates a range of possible modifications of the various aspect, embodiments, and examples described herein. Additionally, it should be understood that the concepts described herein may be employed along or in combination with any of the other embodiments and examples described herein. It should be further appreciated that the various alternatives described above with respect to one illustrated embodiment can apply to all other embodiments and examples described herein, unless otherwise indicated. Reference is therefore made to the claims.

We claim:

1. A layered edible product comprising:

a gummy core;

an inner active layer comprising an inner API (API); and an outer active layer comprising an outer API, wherein the inner API has different constituent components than the outer API.

2. The layered edible product of claim 1, wherein the inner active layer is disposed over the core.

3. The layered edible product of claim 1, wherein the core and the inner active layer defines an edible body, and the layered edible product further comprises a wrapper that covers at least an outermost surface of the edible body.

4. The layered edible product of claim 3, wherein the wrapper is dissolvable by saliva against a sublingual mucosa and a buccal mucosa.

5. The layered edible product of claim 3, wherein the wrapper is configured for removal from the edible body prior to placement of the edible body into the mouth.

6. The layered edible product of claim 3, wherein the wrapper is inert.

7. The layered edible product of claim 1, wherein the inner active layer defines an outermost active layer of the layered edible product.

8. The layered edible product of claim 1, wherein the inner active layer also defines an innermost active layer such that no active layer is disposed between the inner active layer and the core.

9. The layered edible product of claim 7, wherein the inner active layer is the only active layer of the layered edible product.

10. The layered edible product of claim 1, wherein the inner active layer and the outer active layer have different flavor profiles.

11. The layered edible product of claim 1, wherein the inner API has a therapeutic effect configured to last for a different duration than the outer API.

12. The layered edible product of claim 11, wherein the core has a core API that is configured to increase in the bloodstream after the inner API has begun decreasing in the bloodstream.

13. The layered edible product of claim 1, wherein the inner active layer is disposed between the core and the outer active layer.

14. The multilayer edible product of claim 13, wherein the inner and outer active layers are each configured to dissolve against a sublingual mucosa and a buccal mucosa.

15. The layered edible product of claim 1, further comprising a partition layer disposed between the inner and outer active layers.

16. The layered edible product of claim 15, wherein the partition layer is inert.

17. The layered edible product of claim 13, wherein the outer active layer substantially entirely encapsulates the inner active layer.

18. The layered edible product of claim 13, wherein the inner and outer API are configured to last for a shorter time duration in the bloodstream than the core active pharmaceutical ingredient.

19. The layered edible product of claim 13, wherein the core has a core API that is configured to increase in the bloodstream after the inner and outer APIs have begun decreasing in the bloodstream.

20. The layered edible product of claim 1, wherein the inner active layer substantially entirely encapsulates the core.

21. The layered edible product of claim 1, wherein an outer core surface of the core faces the inner active layer, and a core inner surface of the core opposite the outer core surface of the core faces away from the inner active layer.

22. The layered edible of claim 16, wherein the partition layer comprises a respective API.

23. The layered edible product of claim 1, wherein the core is inert.

24. The layered edible product of claim 1, wherein the core has a core API that is different than each of the inner API and the outer API.

25. The layered edible product of claim 1, further comprising a partition layer disposed between the gummy core and the inner active layer.

26. The layered edible product of claim 25, wherein the partition layer is an active partition layer containing a respective API.

27. The layered edible product of claim 25, wherein the partition layer is inert.

28. The layered edible product of claim 25, further comprising a second partition layer disposed between the inner active layer and the outer active layer.

29. The layered edible product of claim 1, wherein the outer active layer comprises a plurality of outer active layers sequentially arranged over the inner active layer.

30. The layered edible product of claim 29, wherein at least some of the outer active layers have the same API.

31. The layered edible product of claim 29, wherein all of the outer active layers have the same API.

32. The layered edible product of claim 29, wherein all of the outer active layers have the same API but in different proportions.

33. The layered edible product of claim 29, wherein at least one of the outer active layers have the same API as the inner API.

34. The layered edible product of claim 29, wherein at least some of the outer active layers have different APIs.

35. The layered edible product of claim 34, wherein all of the outer active layers have different APIs.

* * * * *